(12) United States Patent
Schlingensiepen et al.

(10) Patent No.: US 6,972,171 B1
(45) Date of Patent: Dec. 6, 2005

(54) ANTISENSE OLIGONUCLEOTIDE PREPARATION METHOD

(75) Inventors: Karl-Hermann Schlingensiepen, Göttingen (DE); Wolfgang Brysch, Göttingen (DE)

(73) Assignee: Biognostik Ges. fur biomolekulare Diagnostik mbH, Gottingen (DE)

( * ) Notice: Subject to any disclaimer, the term of this patent is extended or adjusted under 35 U.S.C. 154(b) by 0 days.

(21) Appl. No.: 09/341,700

(22) PCT Filed: Jan. 30, 1998

(86) PCT No.: PCT/EP98/00497

§ 371 (c)(1),
(2), (4) Date: Sep. 24, 1999

(87) PCT Pub. No.: WO98/33904

PCT Pub. Date: Aug. 6, 1998

(30) Foreign Application Priority Data

Jan. 31, 1997 (EP) .............................. 97101531

(51) Int. Cl.[7] .......................... C12Q 1/68; C12P 19/34; C07H 21/02; C07H 21/04
(52) U.S. Cl. ......................... 435/6; 435/91.1; 435/91.5; 536/23.1; 536/24.5
(58) Field of Search .......................... 435/6, 91.1, 91.5, 435/455, 325, 375; 536/23.1, 24.5, 25.3; 514/44

(56) References Cited

U.S. PATENT DOCUMENTS 5,801,154 A * 9/1998 Baracchini et al. ............ 514/44
5,948,888 A * 9/1999 de la Monte et al. ........ 530/350

FOREIGN PATENT DOCUMENTS

| WO | WO90/10030 | 9/1990 |
| WO | WO93/07883 | 4/1993 |
| WO | WO94/25588 | 11/1994 |
| WO | WO95/00103 | 1/1995 |
| WO | WO95/02422 | 1/1995 |
| WO | WO96/31600 | 10/1996 |
| WO | WO96/39415 | 12/1996 |

OTHER PUBLICATIONS

Stull et al. Nucleic Acids Res. (1992) vol. 20, No. 13: 3501–3508.*
Probst et al. Trends in Gen. (1996) vol. 12, No. 8: 290–291.*
Toon F.C.M. Smetsers et al., Sense and Nucleic Acid Drug Development, 6: pp. 63–67.*
Stanley T. Crooke, Therapeutic Applications of Oligonucleotides, Annu. Rev. Pharmacol. Toxicol, 1992, 32, pp. 329–376.*
James, W. Antiviral Chem. and Chemotherapy, vol. 2, No. 4, pp. 191–214, 1991.*
Milner et al. Nature Biotech., vol. 15, pp. 537–541. 1997.*
Ehrlich et al. Antisense Res. and Dev., vol. 4, pp. 173–183, 1994.*
Vaerman et al. Blood, vol. 90, No. 1, pp. 331–339, 1997.*
Branch, A. Trends in Biochem. Sci., vol. 23, pp. 45–50, 1997.*

Crooke, S.T. Antisense Res. and Application, Chapter 1, pp. 1–50, Published by Springer–Verlag, 1998.*
Verma et al. Nature, vol. 389, pp. 239–243, 1997.*
Crystal, R.G. Science, vol. 270, pp. 404–410, 1995.*
Friedmann, T. Scientific American, June Volume, pp. 96–101, 1997.*
Yu et al., "Hybrid Oligonucleotides: Synthesis, Biophysical Properties, Stability Studies, and Biological Activity," *Bioorganic & Medicinal Chemistry*, 4 (10) : 1685–1692 (1996).
Zhao et al., "Effect of Different Chemically Modified Oligodeoxynucleotides on Immune Stimulation," *Biochemical Pharmacology*, 51 (2) : 173–182 (1996).
Hatzfeld, "Release of Early Human Hematopoietic Progenitors from Quiescence by Antisense Transforming Growth Factor β1 or Rb Oligonucleotides," *Journal of Experimental Medicine*, 174 (4) : 925–929 (1991).
Fitzpatrick, et al., "Antisense Oligonucleotides Specific for Transforming Growth Factor β2 Inhibit the Growth of Malignant Mesothelioma Both in Vitro and in Vivo," *Cancer Research*, 57 : 3200–3207 (1997).
Pisetsky et al., "Stimulation of in vitro proliferation of murine lymphocytes by synthetic oligonucleotides, " *Molecular Biology Reports*, 18 (3) :217–221 (1993).
Jachimczak et al., "Transforming growth factor β–mediated autocrine growth regulation of gliomas as detected with phosphorothioate antisense oligonucleotides," *International Journal of Cancer*, 65 (3) :332–337 (1996).
Jachimczak et al., "The effect of transforming growth factor $β_2$–specific phosphorothioate–anti–sense oligonucleotides in reversing cellular immunosuppression in malignant glioma," 78 : 944–951 (1993).
Agrawal, "Antisense oligonucleotides: towards clinical trials," *Trends in Biotechnology*, 14(10) :376–387 (1996).

* cited by examiner

Primary Examiner—Ram R. Shukla
Assistant Examiner—Jane Zara
(74) Attorney, Agent, or Firm—Jacobson Holman PLLC

(57) ABSTRACT

A method for the preparation of an antisense oligonucleotide or derivative thereof comprising the steps of: selecting a target nucleic acid, if necessary elucidating its sequence; generating the antisense oligonucleotide with the proviso that: the oligonucleotide comprises at least 8 residues; the oligonucleotide comprises at maximum twelve elements, which are capable of forming three hydrogen bonds each to cytosine bases; the oligonucleotide does not contain four or more consecutive elements, capable of forming three hydrogen bonds each with four consecutive cytosine bases (CCCC) within the target molecule or alternatively four or more consecutive elements of GGGG; the oligonucleotide does also not contain 2 or more series of three consecutive elements, capable of forming three hydrogen bonds each with three consecutive cytosine bases (CCC) within the target molecule, or alternatively 2 or more series of three consecutive elements of GGG; and the ratio between residues forming two hydrogen bonds per residue (2H-bond-R) with the target molecule and those residues forming three hydrogen bonds per residue (3H-bond-R) with the target molecule, is ruled by the following specifications: 3H-bond-R/3H-bond-R+2H-bond-R ≧ 0.29, and synthesizing the oligonucleotide thus generated in a per se known manner.

9 Claims, 36 Drawing Sheets

Adenine

Guanine

Cytosine

Thymine

FIG. 3-1

Figure 1:
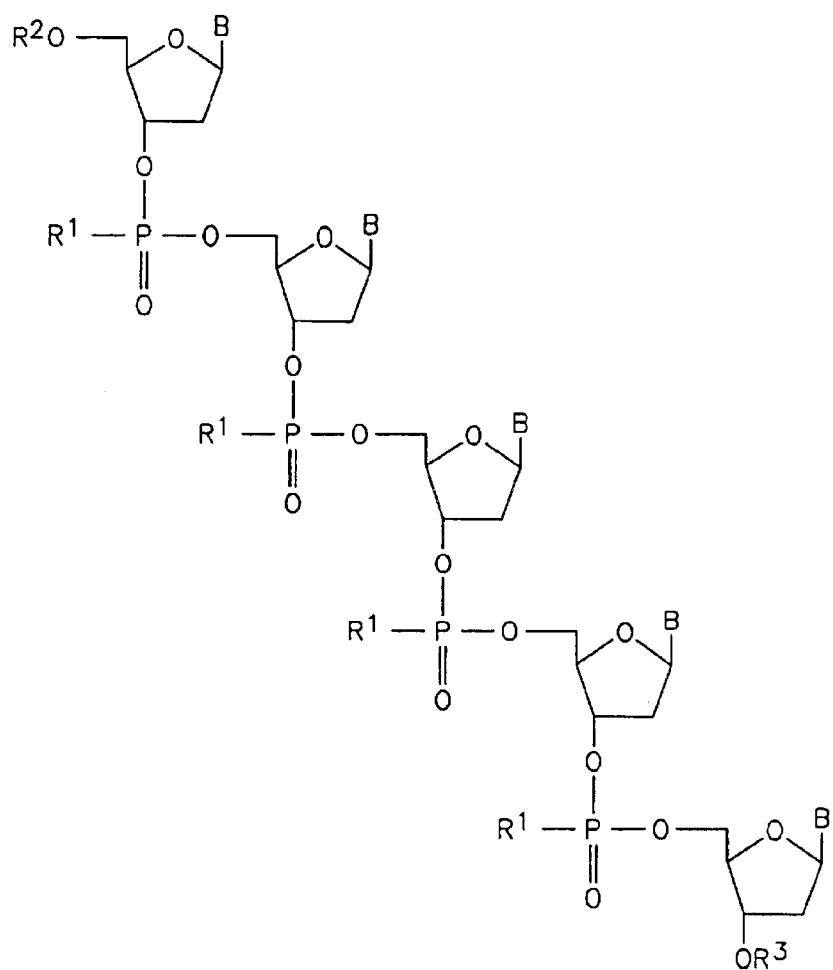
Figure 1:
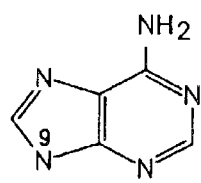
Figure 1:
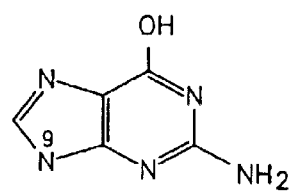
Figure 1:
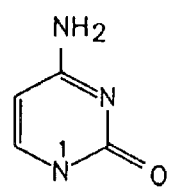
Figure 1:
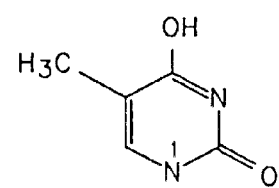

| # | ID | Sequence |
|---|---|---|
| 1. | A3 | CCCGGAGGGCGGCATGGGGGA |
| 2. | N1 | CCTCAGGGAGAAGGGCGC |
| 3. | N2 | GTAGGAGGGCCTCGAGGG |
| 4. | N3 | CTGCAGGGGCTGGGGGTC |
| 5. | N4 | AGGGCTGGTTGTGGTGGGG |
| 6. | N5 | GGCATGGGGGAGGCGGCG |
| 7. | N6 | CCGGAGGGCGGCATGGGG |
| 8. | N7 | GGGGGGCTGGCGAGCCGC |
| 9. | N8 | GGACAGGATCTGGCCGCGGATGG |
| 10. | N9 | CCCCCTGGCTCGGGGGGC |
| 11. | N10 | GGGCCGGGCGGCACCTCC |
| 12. | N11 | GGGCAGCGGGCCGGGCGG |
| 13. | N12 | ACGGCCTCGGGCAGCGGG |
| 14. | N13 | GGGTGCTGTTGTACAGGG |
| 15. | N14 | GGGTTTCCACCATTAGCACGCGGG |
| 16. | N15 | TCATAGATTTCGTT |
| 17. | N16 | TTGTCATAGATTT |
| 18. | N17 | AAGAACATATATATG |
| 19. | N18 | AAGAACATATATAT |
| 20. | N19 | TTGAAGAACATATATA |
| 21. | N20 | CCGGGAGAGCAACACGGG |
| 22. | N21 | ACTTTTAACTTGA |
| 23. | N22 | ATTGTTGCTGTATTT |
| 24. | N23 | ATTGTTGCTGTATT |
| 25. | N24 | AATTGTTGCTGTATT |
| 26. | N25 | AATTGTTGCTGTAT |
| 27. | N26 | GGCGAGTCGCTGGGTGCCAGCAGCCGG |
| 28. | N27 | GGCGAGTCGCTGGG |
| 29. | N28 | ACATCAAAAGATAA |
| 30. | N29 | TGACATCAAAAGAT |
| 31. | N30 | GGGCCCTCTCCAGCGGGG |
| 32. | N31 | GGGCTCGGCGGTGCCGGG |
| 33. | N32 | GGGGCAGGGCCCGAGGCA |
| 34. | N33 | GGCTCCAAATGTAGGGGC |
| 35. | N34 | CGGGTTATGCTGGTTGTACAGGGC |
| 36. | N35 | CGGCGCCGCCGAGGCGCCCGGG |
| 37. | N36 | GGGGCGGGGCGGGACC |
| 38. | N37 | GGGCGGGGCGGGGCGGG |
| 39. | N38 | GGGCGGGGTGGGGCCGGG |
| 40. | N39 | GGCAAGGCAGCGGGGGCGGGG |
| 41. | TGF-β1-1 | CGGTAGCAGCAGCG |
| 42. | TGF-β1-2 | CCAGTAGCCACAGC |
| 43. | TGF-β1-3 | GCAGGTGGATAGTCC |
| 44. | TGF-β1-4 | CTTGCAGGTGGATAG |
| 45. | TGF-β1-5 | CGATAGTCTTGCAGG |
| 46. | TGF-β1-6 | CCATGTCGATAGTCTTGC |
| 47. | TGF-β1-7 | CTCGATGCGCTTCCG |
| 48. | TGF-β1-8 | CCTCGATGCGCTTCC |
| 49. | TGF-β1-9 | GGATGGCCTCGATGC |
| 50. | TGF-β1-10 | GGACAGGATCTGGCC |
| 51. | TGF-β1-11 | CGCAGCTTGGACAGG |
| 52. | TGF-β1-12 | GAGCCGCAGCTTGG |
| 53. | TGF-β1-13 | CGAGCCGCAGCTTG |
| 54. | TGF-β1-14 | ACCTCCCCCTGGCT |
| 55. | TGF-β1-15 | CCACCATTAGCACG |
| 56. | TGF-β1-16 | GAACTTGTCATAGATTTC |
| 57. | TGF-β1-17 | GCTGTGTGTACTCTGC |
| 58. | TGF-β1-18 | GCTCCACGTGCTGC |
| 59. | TGF-β1-19 | GAATTGTTGCTGTATTTC |
| 60. | TGF-β1-20 | GCCAGGAATTGTTGC |
| 61. | TGF-β1-21 | GTGACATCAAAAGATAAC |
| 62. | TGF-β1-22 | GGCTCAACCACTGCC |
| 63. | TGF-β1-23 | GCTGTCACAGGAGC |
| 64. | TGF-β1-24 | CCTGCTGTCACAGG |
| 65. | TGF-β1-25 | GCAGTGTGTTATCCCTGC |
| 66. | TGF-β1-26 | GCAGTGTGTTATCCC |

FIG. 3-2

| # | Name | Sequence |
|---|---|---|
| 67. | TGF-β1-27 | CCAGGTCACCTCGG |
| 68. | TGF-β1-28 | GCCATGAATGGTGGC |
| 69. | TGF-β1-29 | GCCATGAATGGTGG |
| 70. | TGF-β1-30 | CCATGAGAAGCAGG |
| 71. | TGF-β1-31 | GGAAGTCAATGTACAGC |
| 72. | TGF-β1-32 | CCACGTAGTACACGATGG |
| 73. | TGF-β1-33 | GCACTTGCAGGAGC |
| 74. | p53-1 | CCATGGCAGTGACC |
| 75. | p53-2 | GGCTCCTCCATGGC |
| 76. | p53-3 | GCTAGGATCTGACTGC |
| 77. | p53-4 | CCTGACTCAGAGGG |
| 78. | p53-5 | GGTCTGAAAATGTTTCC |
| 79. | p53-6 | CCATTGCTTGGGACGG |
| 80. | p53-7 | GCATCAAATCATCC |
| 81. | p53-8 | CCATTGTTCAATATCG |
| 82. | p53-9 | GGTCTTCAGTGAACC |
| 83. | p53-10 | GGAGCTTCATCTGGACC |
| 84. | p53-11 | CCTCTGGCATTCTGG |
| 85. | p53-12 | AGGGACAGAGATG |
| 86. | p53-13 | GTTTTCTGGGAAGG |
| 87. | p53-14 | GGTTTTCTGGGAAG |
| 88. | p53-15 | AGGTTTCTGGGAAG |
| 89. | p53-16 | GTAGGTTTTCTGGG |
| 90. | p53-17 | GGTAGGTTTTCTGG |
| 91. | p53-18 | CCAGAATGCAAGAAGCC |
| 92. | p53-19 | GCTGTCCCAGAATGC |
| 93. | p53-20 | GCAAGTCACAGACTTGGC |
| 94. | p53-21 | CCACAGCTGCACAGG |
| 95. | p53-22 | GGTGTGGAATCAACC |
| 96. | p53-23 | GTCATGTGCTGTGA |
| 97. | p53-24 | CGCTATCTGAGCAGCG |
| 98. | p53-25 | CCAGTGTGATGATGG |
| 99. | p53-26 | CCAGTAGATTACCACTGG |
| 100. | p53-27 | GGCACAAACACGCACC |
| 101. | p53-28 | CCACGGATCTGAAGG |
| 102. | p53-29 | CGGAACATCTCGAAGCG |
| 103. | p53-30 | CCTCATTCAGCTCTCGG |
| 104. | p53-31 | CCTTGAGTTCCAAGG |
| 105. | p53-32 | CCTTTTTGGACTTCAGG |
| 106. | p53-33 | GGAGGTAGACTGACCC |
| 107. | p52-N-1 | AAAATGTTTCCT |
| 108. | p52-N-2 | TGAAAATGTTTC |
| 109. | p52-N-3 | CTGAAAATGTTT |
| 110. | p52-N-4 | TCTGAAAATGTTT |
| 111. | p52-N-5 | TCTGAAAATGTT |
| 112. | p52-N-6 | AAATCATCCATT |
| 113. | p52-N-7 | TTGTTCAATATC |
| 114. | p52-N-8 | ATTGTTCAATATC |
| 115. | p52-N-9 | ATTGTTCAATAT |
| 116. | p52-N-10 | CATTGTTCAATAT |
| 117. | p52-N-11 | CATTGTTCAATA |
| 118. | p52-N-12 | AAAAGTGTTCT |
| 119. | p52-N-13 | ACATGATTTTTAT |
| 120. | p52-N-14 | AACATGAGTTTTTAT |
| 121. | p52-N-15 | ACATGAGTTTTTA |
| 122. | p52-N-16 | AACATGAGTTTTTA |
| 123. | p52-N-17 | AACATGAGTTTTTT |
| 124. | p52-N-18 | AAAACATCTTGTT |
| 125. | p53-T-1 | CAGAGGGGGCTCGACGC |
| 126. | p53-T-2 | CTGACTCAGAGGGGGCTC |
| 127. | p53-T-3 | AGGGGGACAGAACG |
| 128. | p53-T-4 | TTGGGACGGCAAGGGGGACAGAA |
| 129. | p53-T-5 | TGGGACGGCAAGGGGGA |

FIG. 3-3

| # | Name | Sequence |
|---|------|----------|
| 130. | p53-T-6 | GCCACGGGGGGAGCA |
| 131. | p53-T-7 | GCAGGGGCCACGGGGGGAG |
| 132. | p53-T-8 | AGGGGCCACGGGGG |
| 133. | p53-T-9 | CAGGGGCCACGGGG |
| 134. | p53-T-10 | GGTGCAGGGGCCACG |
| 135. | p53-T-11 | TGGTGCAGGGGCCGCCGG |
| 136. | p53-T-12 | GGGGCTGGTGCAGGGGCC |
| 137. | p53-T-13 | AGGGGGCTGGTGCAGGGG |
| 138. | p53-T-14 | GGGCTGGTGCAGGG |
| 139. | p53-T-15 | GAGGGGGCTGGTGCAG |
| 140. | p53-T-16 | AGGAGGGGCTGGTG |
| 141. | p53-T-17 | GGGCCAGGAGGGGGCTGG |
| 142. | p53-T-18 | AGGGGCCAGGAGGGGGCT |
| 143. | p53-T-19 | GGGGCCAGGAGGGG |
| 144. | p53-T-20 | CAGGGGCCAGGAGGG |
| 145. | p53-T-21 | TCTGGGAAGGGACAGA |
| 146. | p53-T-22 | TGAGGGCAGGGCAGTA |
| 147. | p53-T-23 | TTGAGGGCAGGGGAG |
| 148. | p53-T-24 | CGGGTGCCGGGCGGGGGTG |
| 149. | p53-T-25 | CGGACGCGGGTGCCGGGCGGGGGT |
| 150. | p53-T-26 | CGGGTGCCGGGCGGG |
| 151. | p53-T-27 | GGACGCGGGTGCCGGGCG |
| 152. | p53-T-28 | TGGGGGCAGCGCCTCACA |
| 153. | p53-T-29 | GGTGGGGGCAGCGCCT |
| 154. | JunB-1 | CCATTTTAGTGCACATCCGG |
| 155. | JunB-2 | CCATTTTAGTGCACATCC |
| 156. | JunB-3 | GCTGTTCCATTTTAGTGC |
| 157. | JunB-4 | GTAGTCGTGTAGAG |
| 158. | JunB-5 | GTTTGTAGTCGTGTAG |
| 159. | JunB-6 | GTTTCAGGAGTTTGTAG |
| 160. | JunB-7 | CCAGCTCCGAAGAGG |
| 161. | JunB-8 | CGTCGTCGTGATCACG |
| 162. | JunB-9 | GGTAAAAGTACTGTTCC |
| 163. | JunB-10 | GGCTTTGACAAAGCC |
| 164. | JunB-11 | CTTGTGCAGATCGTCCAG |
| 165. | JunB-12 | CGTGGTTCATCTTGTGC |
| 166. | JunB-13 | CACGTGGTTCATCTTGTG |
| 167. | JunB-14 | CCTCCTTGAAGGTGG |
| 168. | JunB-15 | CGCTCCACTTTGATGCG |
| 169. | JunB-16 | CCTTGTCCTCCAGG |
| 170. | JunB-17 | GGTACTCGACAGCC |
| 171. | JunB-18 | CTGACGTGGGTCATG |
| 172. | JunB-19 | CCGTTGCTGACGTGG |
| 173. | JunD-1 | CATCCTCCGCCTCC |
| 174. | JunD-2 | GTTTCCATCCTCCG |
| 175. | JunD-3 | GGTGTTCCATCCTCC |
| 176. | JunD-4 | GGTGTTTCCATCCTC |
| 177. | JunD-5 | GCTCAGCGCCTCATC |
| 178. | JunD-6 | CCTTCTTCATCATGCTGC |
| 179. | JunD-7 | CCTTCTTCATCATGCTG |
| 180. | JunD-8 | CCTTCTTCATCATGC |
| 181. | JunD-9 | GCGTCCTTCTTCATCATGC |
| 182. | JunD-10 | CCTGCTCACTCAGG |
| 183. | JunD-11 | CGCAGGCTTGAGCG |
| 184. | JunD-12 | GCCAGCTTCAGCAGC |
| 185. | JunD-13 | GGTGGTGACCAGCC |
| 186. | JunD-14 | CCTCGGCGAACTCC |
| 187. | JunD-15 | GCTTGTGTAAATCC |
| 188. | JunD-16 | GGTTCTGCTTGTGTAAATCC |
| 189. | JunD-17 | GCTGCTCAGGTTCGC |
| 190. | JunD-18 | GAAGGCGACCGTCG |
| 191. | JunD-19 | CGAAGGCCACCGTC |
| 192. | JunD-20 | GCACCGTCTGTGCC |
| 193. | JunD-21 | CGTGTCCATGTCGATGG |
| 194. | JunD-22 | CGTGTCCATGTCGATG |

FIG. 3-4

| | | |
|---|---|---|
| 195. | JunD-23 | GCGTGTCCATGTCG |
| 196. | JunD-24 | CCAGCTTGCGCTTGC |
| 197. | JunD-25 | CGCTCCAGCTTGCG |
| 198. | JunD-26 | CGTGTTCTGACTCTTGAG |
| 199. | JunD-27 | CGTGTTCTGACTCTTG |
| 200. | JunD-28 | GCTGTTGACGTGGC |
| 201. | JunD-29 | CGACTCAGTACGCC |
| 202. | JunD-30 | GCCATGCCCGACTC |
| 203. | JunD-31 | CCCTTGGAGGTGGC |
| 204. | JunB-N-1 | TTTTAGTGCACAT |
| 205. | JunB-N-2 | TGTTCCATTTTAGT |
| 206. | JunB-N-3 | AAAAAAAGTGGAAG |
| 207. | JunB-N-4 | TACAAAAAAAAGTG |
| 208. | JunB-N-5 | ATACAAAAAAAAGT |
| 209. | JunB-N-6 | CATACAAAAAAAAGT |
| 210. | JunB-N-7 | CATACAAAAAAAAG |
| 211. | JunB-N-8 | GAAAAAAAACATAC |
| 212. | JunB-N-9 | CAGAAAAAAAAACATAC |
| 213. | JunB-N-10 | CAGAAAAAAAAACAT |
| 214. | JunB-N-11 | TTCAATATGAATCG |
| 215. | JunB-N-12 | TATTCAATATGAATCG |
| 216. | JunB-N-13 | TATTCAATATGAATC |
| 217. | JunB-N-14 | TATTCAATATGAAT |
| 218. | JunB-N-15 | TATATTCAATATGAA |
| 219. | JunB-N-16 | TTATATTCAATATGA |
| 220. | JunB-N-17 | TATTATATTCAATATGA |
| 221. | JunB-N-18 | TTATATTCAATATG |
| 222. | JunB-N-19 | TATTATATTCAATATG |
| 223. | JunB-N-20 | ATTATATTCAATAT |
| 224. | JunB-N-21 | TATTATATTCAATAT |
| 225. | JunB-N-22 | ATATATTATATTCAATAT |
| 226. | JunB-N-23 | AAATATATTATATTCAATAT |
| 227. | JunB-N-24 | TATTATATTCAATA |
| 228. | JunB-N-25 | ATATATTATATTCAATA |
| 229. | JunB-N-26 | CAAATATATTATATTCAATA |
| 230. | JunB-N-27 | TATATTATATTCAAT |
| 231. | JunB-N-28 | AATATATTATATTCAAT |
| 232. | JunB-N-29 | TATATTATATTCAA |
| 233. | JunB-N-30 | CAAATATATTATATTCAA |
| 234. | JunB-N-31 | CAAATATATTATATTCA |
| 235. | JunB-N-32 | CAAATATATTATATTC |
| 236. | JunB-N-33 | CACAAATATATTATATTC |
| 237. | JunB-N-34 | AAATATATTATATT |
| 238. | JunB-N-35 | CAAATATATTATATT |
| 239. | JunB-N-36 | CAAATATATTATAT |
| 240. | JunB-N-37 | CACAAATATATTATAT |
| 241. | JunB-N-38 | CACAAATATATTAT |
| 242. | JunB-N-39 | TACACAAATATATTAT |
| 243. | JunB-N-40 | TACACAAATATATTA |
| 244. | JunB-N-41 | TAAATACACAAATATATT |
| 245. | JunB-N-42 | AATACACAAATATA |
| 246. | JunB-N-43 | GTTAAATACACAAATA |
| 247. | JunB-N-44 | TGTTAAATACACAA |
| 248. | JunB-N-45 | TTTAGAGACTAAGT |
| 249. | JunB-N-46 | ATAAACTCTTTAGA |
| 250. | JunB-N-47 | TAAAATAAACTCTTTAG |
| 251. | JunB-N-48 | TAAAATAAACTCTTTA |
| 252. | JunB-N-49 | TTAAAATAAACTCTTT |
| 253. | JunB-N-50 | CTTAAAATAAACTC |
| 254. | JunB-N-51 | TAAAAAGAACAAACA |
| 255. | JunB-N-52 | TAAAAAAGAACAAAC |
| 256. | JunB-N-53 | CAATAAAAAGAACAA |
| 257. | JunB-N-54 | TCAATAAAAAGAACAA |
| 258. | JunB-N-55 | TCAATAAAAAGAAC |
| 259. | JunB-N-56 | TTCAATAAAAAGAA |
| 260. | JunB-N-57 | TAGATTCAATAAAAAGA |

FIG. 3-5

| # | Name | Sequence |
|---|---|---|
| 261. | JunB-T-1 | TGGCGCGGGCGGGTAGC |
| 262. | JunB-T-2 | GGGCTGGCGGCGGGCGGGTAG |
| 263. | JunB-T-3 | TCGGGGGCTGGCGCGGGCGGG |
| 264. | JunB-T-4 | TGGGTGCCTGGTCGCGCGTTCTCGGG |
| 265. | JunB-T-5 | AGGGTCCCTGCGGGGCCG |
| 266. | JunB-T-6 | GGGAGGGTCCCTGCGGGG |
| 267. | JunB-T-7 | GGGAGGGTCCCTGCGG |
| 268. | JunB-T-8 | TGGGCCGGGTCCGC |
| 269. | JunB-T-9 | TCCCGGGGGTGTAG |
| 270. | JunB-T-10 | AGTACTGTCCCGGGGGTGT |
| 271. | JunB-T-11 | GGGACACGTTGGGGGGTG |
| 272. | JunB-T-12 | GCCGGGGGGCCCCCGGTAGC |
| 273. | JunB-T-13 | CGGGCCCAGCCGGGGGC |
| 274. | JunB-T-14 | CGGGCCCAGCCGGG |
| 275. | JunB-T-15 | GGGAGGTGGCTCCGGGCCGG |
| 276. | JunB-T-16 | AGGGCGGCGCGTGTGGGA |
| 277. | JunB-T-17 | GGGTGGCCACCGGCGAAGGG |
| 278. | JunB-T-18 | AGGGGCAGGGGACGT |
| 279. | JunB-T-19 | TAAAGGGGCAGGGGACGT |
| 280. | JunB-T-20 | AGGGGGTGTCCGTAAAGGGG |
| 281. | JunD-T-1 | GGGGACGCGAACGTGCCGCCG |
| 282. | JunD-T-2 | CGGGGAACAAGCGGCCCCGGGG |
| 283. | JunD-T-3 | GGCCGTCGGGGGCG |
| 284. | JunD-T-4 | GCGGCCGTCGGGGGGC |
| 285. | JunD-T-5 | AGGGGGGTAGGAGGCGGG |
| 286. | JunD-T-6 | GCGCTGGGGGCGCC |
| 287. | JunD-T-7 | GGCCGTCGGGGGGT |
| 288. | JunD-T-8 | GGGGAGGCCAGCTTC |
| 289. | JunD-T-9 | GGCCGCCACCTTGGGG |
| 290. | JunD-T-10 | GCGGCCGCCGCCGGGG |
| 291. | JunD-T-11 | GGGCGCGGCCGCCCCGCCGGGG |
| 292. | JunD-T-12 | GGGGTGGCGGCGGCGG |
| 293. | JunD-T-13 | GGGGGTGGCGGCGGC |
| 294. | JunD-T-14 | TGGGGCAGCAGCTGGCAG |
| 295. | JunD-T-15 | CGGGGCGCCCACGACACC |
| 296. | JunD-T-16 | CGGGGCGCCCACGACAC |
| 297. | JunD-T-17 | GGGCCGCACCCTCTCCAAGTCCGGGG |
| 298. | ErbB-2-1 | GCAGCAGTCAGTGG |
| 299. | ErbB-2-2 | CCATTGTCTAGCACGG |
| 300. | ErbB-2-3 | GGTCTCCATTGTCTAGC |
| 301. | ErbB-2-4 | GGTGGTATTGTTCAGC |
| 302. | ErbB-2-5 | GCTGGATCAAGACCC |
| 303. | ErbB-2-6 | CCACAAAATCGTGTCC |
| 304. | ErbB-2-7 | CCTTCCACAAAATCGTGTCC |
| 305. | ErbB-2-8 | GGTTGTTCTTGTGG |
| 306. | ErbB-2-9 | CCTCTTGGTTGTGC |
| 307. | ErbB-2-10 | CCAGAGTCTCAAACACTTGG |
| 308. | ErbB-2-11 | GGTAACCTGTGATCTCTTCC |
| 309. | ErbB-2-12 | CCTGCAGTACTCGG |
| 310. | ErbB-2-13 | GGCATTCACATACTCC |
| 311. | ErbB-2-14 | GCAAACAGTGCCTGGC |
| 312. | ErbB-2-15 | CGCATCGTGTACTTCCG |
| 313. | ErbB-2-16 | GCACGTTCCGAGCG |
| 314. | ErbB-2-17 | GGTACCAGATACTCC |
| 315. | ErbB-2-18 | CCAGTGGAGACCTGG |
| 316. | ErbB-2-19 | CCTGAGGACACATCAGG |
| 317. | ErbB-2-20 | CCTCACTTGGTTGTGAGC |
| 318. | ErbB-2-21 | GGAAGATGTCCTTCC |
| 319. | ErbB-2-22 | GCACACTGCTCATGGC |
| 320. | ErbB-2-23 | GCTGTCACCTCTTGG |
| 321. | ErbB-2-24 | CCTCTGCTGTCACC |
| 322. | ErbB-2-25 | CCACACATCACTCTGG |
| 323. | ErbB-2-26 | CCTCCTCTTCAGAGG |

FIG. 3-6

| # | Name | Sequence |
|---|------|----------|
| 324. | ErbB-2-27 | CCTTCTGGTTCACACTGG |
| 325. | ErbB-2-28 | CATGGTGCTCACTGCG |
| 326. | ErbB-2-29 | CTTGGTTGTGAGCG |
| 327. | ErbB-2-30 | GGACAGGCAGTCAC |
| 328. | ErbB-2-31 | GTCACCTCTTGGTTGTGC |
| 329. | ErbB-2-32 | CCAGAGTCTCAAACAC |
| 330. | ErbB-2-33 | CACATACTCCCTGG |
| 331. | ErbB-2-34 | GACCAGCACGTTCCG |
| 332. | ErbB-2-35 | GTTGGTGTCTATCAGTG |
| 333. | ErbB-2-36 | CCCTGGTAGAGGTG |
| 334. | ErbB-2-37 | CTCAAACACTTGGAGC |
| 335. | ErbB-2-38 | CACACATCACTCTGGTGG |
| 336. | ErbB-2-39 | GCACAGACAGTGCGC |
| 337. | ErbB-2-40 | CATGGCAGCAGTCAG |
| 338. | ErbB-2-41 | CTGCTCATGGCAGCAG |
| 339. | ErbB-2-42 | CATCTGGAAACTTCCAGATG |
| 340. | ErbB-2-43 | CTGGAAACTTCCAG |
| 341. | ErbB-2-44 | CATAACTCCACACATCACTC |
| 342. | ErbB-2-45 | CACCATAACTCCACACATC |
| 343. | ErbB-2-46 | CTGGTGGGTGAACC |
| 344. | ErbB-2-47 | CGGATTACTTGCAGG |
| 345. | ErbB-2-48 | CGCTAGGTGTCAGCG |
| 346. | ErbB-2-49 | GCCATCACGTATGC |
| 347. | ErbB-2-50 | GCATACACCAGTTCAGC |
| 348. | ErbB-2-51 | CCATCAAATACATCGG |
| 349. | ErbB-2-52 | CCAGCAGAAGTCAGG |
| 350. | ErbB-2-53 | GCTTCATGTCTGTGC |
| 351. | ErbB-2-54 | GGTGAGTTCCAGGTTTCC |
| 352. | ErbB-2-55 | CCACAAAATCGTGTCCTGG |
| 353. | ErbB-2-56 | CCCTTACACATCGG |
| 354. | ErbB-2-57 | GCAGCTCACAGATGC |
| 355. | ErbB-2-58 | GCACTGGTAACTGC |
| 356. | ErbB-2-59 | CCTGCATATTGGCACTGG |
| 357. | ErbB-2-60 | CCAGCAAACTCCTGG |
| 358. | ErbB-2-61 | GCAGAAATGCCAGGC |
| 359. | ErbB-2-62 | CCATTGTGCAGAATTCG |
| 360. | ErbB-2-63 | CCCTGCAGTACTCGG |
| 361. | ErbB-2-64 | GGCATTCACATACTCCC |
| 362. | ErbB-2-65 | GGTCAGGTTTCACACC |
| 363. | ErbB-2-66 | CCAGGTCCACACAGG |
| 364. | ErbB-2-67 | CCTTGTCATCCAGG |
| 365. | ErbB-2-68 | GGATCCCAAAGACC |
| 366. | ErbB-2-69 | CCTCAACACTTTGATGG |
| 367. | ErbB-2-70 | GCTGTGTCACCAGC |
| 368. | ErbB-2-71 | GGTCTAAGAGGCAGCC |
| 369. | ErbB-2-72 | GGCAATCTGCATACACC |
| 370. | ErbB-2-73 | CCTGTGTACGAGCC |
| 371. | ErbB-2-74 | CCATCCACTTGATGG |
| 372. | ErbB-2-75 | CCCACACAGTCACACC |
| 373. | ErbB-2-76 | CCATCGTAAGGTTTGG |
| 374. | ErbB-2-77 | CCTTTTCCAGCAGG |
| 375. | ErbB-2-78 | GGAGAATTCAGACACC |
| 376. | ErbB-2-79 | CCAAGTCCTCATTCTGG |
| 377. | ErbB-2-80 | CCATCAGTCTCAGAGG |
| 378. | ErbB-2-81 | CCTTTGAAGGTGCTGG |
| 379. | ErbB-2-82 | GGCATGGCAGGTTCC |
| 380. | ErbB-2-83 | CCTGGCATGGCAGG |
| 381. | ErbB-2-N-1 | AGATGTATAGGTAA |
| 382. | ErbB-2-N-2 | ATTTTCACATTCTC |
| 383. | ErbB-2-N-3 | AATTTTCACATTCTC |
| 384. | ErbB-2-N-4 | AATTTTCACATTCT |
| 385. | ErbB-2-N-5 | GAATTTTCACATTC |
| 386. | ErbB-2-N-6 | GGAATTTTCACATT |
| 387. | ErbB-2-N-7 | AGATTTCTTTGTTG |
| 388. | ErbB-2-N-8 | AAGATTTCTTTGTTG |
| 389. | ErbB-2-N-9 | AAGATTTCTTTGTT |

FIG. 3-7

| # | Name | Sequence |
|---|---|---|
| 390. | ErbB-2-N-10 | TAAGATTTCTTTGTT |
| 391. | ErbB-2-N-11 | CTAAGATTTCTTTGTT |
| 392. | ErbB-2-N-12 | TAAGATTTCTTTGT |
| 393. | ErbB-2-N-13 | CTAAGATTTCTTTGT |
| 394. | ErbB-2-N-14 | CTAAGATTTCTTTG |
| 395. | ErbB-2-N-15 | TCTAAGATTTCTTT |
| 396. | ErbB-2-N-16 | GTCTAAGATTTCTTT |
| 397. | ErbB-2-N-17 | GTCTAAGATTTCTT |
| 398. | ErbB-2-N-18 | TTCGTCTAAGATTT |
| 399. | ErbB-2-N-19 | ATTTTGACATGGTT |
| 400. | ErbB-2-N-20 | AATTTTGACATGGTT |
| 401. | ErbB-2-N-21 | AATTTTGACATGGT |
| 402. | ErbB-2-N-22 | TAATTTTGACATGGT |
| 403. | ErbB-2-N-23 | TAATTTTGACATGG |
| 404. | ErbB-2-N-24 | GTAATTTTGACATG |
| 405. | ErbB-2-N-25 | TGTAATTTTGACATG |
| 406. | ErbB-2-N-26 | TGTAATTTTGACAT |
| 407. | ErbB-2-N-27 | TCTGTAATTTTGACAT |
| 408. | ErbB-2-N-28 | CTGTAATTTTGACA |
| 409. | ErbB-2-N-29 | TCTGTAATTTTGACA |
| 410. | ErbB-2-N-30 | TCTGTAATTTTGAC |
| 411. | ErbB-2-N-31 | GTCTGTAATTTTGA |
| 412. | ErbB-2-N-32 | AAGTCTGTAATTTTGA |
| 413. | ErbB-2-N-33 | AGTCTGTAATTTTG |
| 414. | ErbB-2-N-34 | AAGTCTGTAATTTTG |
| 415. | ErbB-2-N-35 | AAGTCTGTAATTTT |
| 416. | ErbB-2-N-36 | GAAGTCTGTAATTTT |
| 417. | ErbB-2-N-37 | GAAGTCTGTAATTT |
| 418. | ErbB-2-N-38 | ATGTAGACATCAAT |
| 419. | ErbB-2-N-39 | ATCATCCAACATTT |
| 420. | ErbB-2-N-40 | AATCATCCAACATTT |
| 421. | ErbB-2-N-41 | AATCATCCAACATT |
| 422. | ErbB-2-N-42 | ACCATCAAATACAT |
| 423. | ErbB-2-N-43 | AAAAACGTCTTTGA |
| 424. | ErbB-2-N-44 | TTTTGTTCTTAGACA |
| 425. | ErbB-2-N-45 | TTTTGTTCTTAGAC |
| 426. | ErbB-2-N-46 | TAAACAGAAAAGCA |
| 427. | ErbB-2-N-47 | ACTAAACAGAAAAG |
| 428. | ErbB-2-N-48 | AAACTAAACAGAAAAG |
| 429. | ErbB-2-N-49 | AACTAAACAGAAAA |
| 430. | ErbB-2-N-50 | AAACTAAACAGAAAA |
| 431. | ErbB-2-N-51 | AAACTAAACAGAAA |
| 432. | ErbB-2-N-52 | TAAAAACTAAACAGAAA |
| 433. | ErbB-2-N-53 | AAAACTAAACAGAA |
| 434. | ErbB-2-N-54 | GTAAAAACTAAACAGAA |
| 435. | ErbB-2-N-55 | AAAAACTAAACAGA |
| 436. | ErbB-2-N-56 | TAAAAACTAAACAGA |
| 437. | ErbB-2-N-57 | TAAAAACTAAACAG |
| 438. | ErbB-2-N-58 | GTAAAAACTAAACA |
| 439. | ErbB-2-N-59 | AAAAAGTAAAAACTAAACA |
| 440. | ErbB-2-N-60 | AGTAAAAACTAAAC |
| 441. | ErbB-2-N-61 | AAAAAAGTAAAAACTAAAC |
| 442. | ErbB-2-N-62 | AAGTAAAAACTAAA |
| 443. | ErbB-2-N-63 | AAAAAAAGTAAAAACTAAA |
| 444. | ErbB-2-N-64 | AAAGTAAAAACTAA |
| 445. | ErbB-2-N-65 | AAAAGTAAAAACTA |
| 446. | ErbB-2-N-66 | AAAAAAAGTAAAAACTA |
| 447. | ErbB-2-N-67 | AAAAAGTAAAAACT |
| 448. | ErbB-2-N-68 | AAAAAAAGTAAAAACT |
| 449. | ErbB-2-N-69 | AAAAAAAGTAAAAAC |
| 450. | ErbB-2-N-70 | CAAAAAAAGTAAAAAC |
| 451. | ErbB-2-N-71 | AAAAAAAAGTAAAAA |
| 452. | ErbB-2-N-72 | CAAAAAAAGTAAAA |
| 453. | ErbB-2-N-73 | AACAAAACAAAAAAAGTAAA |
| 454. | ErbB-2-N-74 | AAACAAAAAAAGTA |
| 455. | ErbB-2-N-75 | CAAAACAAAAAAAGTA |
| 456. | ErbB-2-N-76 | CAAAACAAAAAAAGT |

FIG. 3-8

| | | |
|---|---|---|
| 457. | ErbB-2-77 | CAAAACAAAAAAAG |
| 458. | ErbB-2-78 | CTTTAAAAAAACAAAAC |
| 459. | ErbB-2-79 | TCTTTAAAAAAACAAA |
| 460. | ErbB-2-80 | GTCTTTAAAAAAACAAA |
| 461. | ErbB-2-81 | GTCTTTAAAAAAACA |
| 462. | ErbB-2-82 | GTCTTTAAAAAAAC |
| 463. | ErbB-2-83 | TTTATTTCGTCTTT |
| 464. | ErbB-2-84 | TCTTTATTTCGTCT |
| 465. | ErbB-2-85 | TATTTGCAAATGGA |
| 466. | ErbB-2-86 | TATATTTGCAAATGG |
| 467. | ErbB-2-87 | TATATTTGCAAATG |
| 468. | ErbB-2-88 | CAAAATATATTTGCAAATG |
| 469. | ErbB-2-89 | CAAAATATATTTGCAAAT |
| 470. | ErbB-2-90 | CAAAATATATTTGCA |
| 471. | ErbB-2-91 | CAAAATATATTTGC |
| 472. | ErbB-2-92 | TTCCAAAATATATTG |
| 473. | ErbB-2-93 | TTTTCCAAAATATATTT |
| 474. | ErbB-2-94 | GTTTTCCAAAATATATT |
| 475. | ErbB-2-95 | GTTTTCCAAAATAT |
| 476. | c-fos-1 | GGTTAGGCAAAGCC |
| 477. | c-fos-2 | CCGAGAACATCATCGTGG |
| 478. | c-fos-3 | CCGAGAACATCATCGTG |
| 479. | c-fos-4 | CCGAGAACATCATCG |
| 480. | c-fos-5 | CGTAGTCTGCGTTGAAGC |
| 481. | c-fos-6 | CCATGCTGGAGAAGG |
| 482. | c-fos-7 | CCGTGCAGAAGTCC |
| 483. | c-fos-8 | GGAATGAAGTTGGC |
| 484. | c-fos-9 | TGACCGTGGGAATG |
| 485. | c-fos-10 | TGGCAGTGACCGTG |
| 486. | c-fos-11 | AGATGGCAGTGACC |
| 487. | c-fos-12 | CGAGATGGCAGTGACC |
| 488. | c-fos-13 | CCAGCCACTGCAGG |
| 489. | c-fos-14 | GCACCAGCCACTGC |
| 490. | c-fos-15 | CCCTGGAGTAAGCC |
| 491. | c-fos-16 | GGAGATAACTGTTCCACC |
| 492. | c-fos-17 | GGAGATAACTGTTCC |
| 493. | c-fos-18 | CTTCTAGTTGGTCTG |
| 494. | c-fos-19 | CATCTTCTAGTTGG |
| 495. | c-fos-20 | TCTCATCTTCTAGTTGG |
| 496. | c-fos-21 | CTGCAAAGCAGACTTCTC |
| 497. | c-fos-22 | CCTTCAGCAGGTTGG |
| 498. | c-fos-23 | CCCAGGTCATCAGG |
| 499. | c-fos-24 | CCAGTCAGATCAAGG |
| 500. | c-fos-25 | GGTGAAGGCCTCCTC |
| 501. | c-fos-26 | CAGGGTGAAGGCCTC |
| 502. | c-fos-27 | CCTGGATGATGCTGG |
| 503. | c-fos-28 | CCACTGTGCAGAGG |
| 504. | c-fos-29 | GGAGTACAGGTGACC |
| 505. | c-fos-30 | GCTCATTGCTGCTGC |
| 506. | c-fos-31 | GGAAGGCTCATTGCTGC |
| 507. | c-fos-N-1 | TTTTCTCTTCTTCT |
| 508. | c-fos-N-2 | ATCTTATTCCTTTC |
| 509. | c-fos-N-3 | CATCTTATTCCTTT |
| 510. | c-fos-N-4 | TAGTTTTTCCTTCT |
| 511. | c-fos-N-5 | TCTAGTTTTTCCTT |
| 512. | c-fos-N-6 | AACTCTAGTTTTTC |
| 513. | c-fos-N-7 | GAACTCTAGTTTTT |
| 514. | c-fos-N-8 | TGAACTCTAGTTTTT |
| 515. | c-fos-N-9 | ATGAACTCTAGTTTTT |
| 516. | c-fos-N-10 | TGAACTCTAGTTTT |
| 517. | c-fos-N-11 | ATGAACTCTAGTTTT |
| 518. | c-fos-N-12 | ATGAACTCTAGTTT |
| 519. | TGF-B2-1 | GCACACAGTAGTGC |

FIG. 3-9

| | | |
|---|---|---|
| 520. | TGF-B2-2 | GCAGGATCAGAAAAGC |
| 521. | TGF-B2-3 | GCAGGTAGACAGGC |
| 522. | TGF-B2-4 | GCTTGCTCAGGATCTGC |
| 523. | TGF-B2-5 | GCAAGTCCCTGGTGC |
| 524. | TGF-B2-6 | CCTGGAGCAAGTCC |
| 525. | TGF-B2-7 | CGTAGTACTCTTCGTCG |
| 526. | TGF-B2-8 | CGTAGTACTCTTCG |
| 527. | TGF-B2-9 | GTAAACCTCCTTGG |
| 528. | TGF-B2-10 | GTCTATTTTGTAAACCTCC |
| 529. | TGF-B2-11 | GCATGTCTATTTTGTAAACC |
| 530. | TGF-B2-12 | GGCATCAAGGTACCC |
| 531. | TGF-B2-13 | GGCATCAAGGTACC |
| 532. | TGF-B2-14 | GCTTTCACCAAATTGGAAGC |
| 533. | TGF-B2-15 | GAGAATCTGATATAGCTC |
| 534. | TGF-B2-16 | GGAGATGTTAAATCTTTGG |
| 535. | TGF-B2-17 | GCTGTCGATGTAGC |
| 536. | TGF-B2-18 | CCAGGTTCCTGTCTTTATGG |
| 537. | TGF-B2-19 | CAGCAGGGACAGTG |
| 538. | TGF-B2-20 | CTTGCTTCTAGTTCTTCAC |
| 539. | TGF-B2-21 | GCCATCAATACCTGC |
| 540. | TGF-B2-22 | GGTGCCATCAATACC |
| 541. | TGF-B2-23 | CCACTGGTATATGTGG |
| 542. | TGF-B2-24 | GGACTTTATAGTTTTCTG |
| 543. | TGF-B2-25 | CTCAAGTCTGTAGGAG |
| 544. | TGF-B2-26 | GGTCTGTTGTGACTC |
| 545. | TGF-B2-27 | CAATTATCCTGCACATTTC |
| 546. | TGF-B2-28 | GCAGCAATTATCCTGC |
| 547. | TGF-B2-29 | GGCAGCAATTATCC |
| 548. | TGF-B2-30 | GGTTCGTGTATCCATTTCC |
| 549. | TGF-B2-31 | GCACAGAAGTTGGC |
| 550. | TGF-B2-32 | CCAGCACAGAAGTTGG |
| 551. | TGF-B2-33 | GTGCTGAGTGTCTG |
| 552. | TGF-B2-34 | CCTGCTGTGCTGAGTG |
| 553. | TGF-B2-35 | GCTCAGGACCCTGC |
| 554. | TGF-B2-36 | GCAGCAAGGGAAGC |
| 555. | TGF-B2-37 | CCAATGTAGTAGAGAATGG |
| 556. | TGF-B2-38 | GCTGCATTTGCAAG |
| 557. | TGF-B2-N-1 | AAAAAAGAAATCAA |
| 558. | TGF-B2-N-2 | AAAAAAAGAAATCAA |
| 559. | TGF-B2-N-3 | AAAAAAAAGAAATCAA |
| 560. | TGF-B2-N-4 | TAAAAAAAAGAAATCAA |
| 561. | TGF-B2-N-5 | ATAAAAAAAAGAAATCAA |
| 562. | TGF-B2-N-6 | AATAAAAAAAAGAAATCAA |
| 563. | TGF-B2-N-7 | GAATAAAAAAAAGAAAT |
| 564. | TGF-B2-N-8 | AGAATAAAAAAAAGAAAT |
| 565. | TGF-B2-N-9 | CAGAATAAAAAAAA |
| 566. | TGF-B2-N-10 | TCAGAATAAAAAAAA |
| 567. | TGF-B2-N-11 | TTGTTTTTAAAAGT |
| 568. | TGF-B2-N-12 | AGTTGTTTTTAAAA |
| 569. | TGF-B2-N-13 | AAGTTGTTTTTAAAA |
| 570. | TGF-B2-N-14 | AAAGTTGTTTTTAAAA |
| 571. | TGF-B2-N-15 | AAAAGTTGTTTTTAAAA |
| 572. | TGF-B2-N-16 | AAAAAGTTGTTTTTAAAA |
| 573. | TGF-B2-N-17 | AAAAAAGTTGTTTTTAAAA |
| 574. | TGF-B2-N-18 | AAAAAAAGTTGTTTTTAAAA |
| 575. | TGF-B2-N-19 | AAAAAAAAGTTGTTTTTAA |
| 576. | TGF-B2-N-20 | TTTTTAAAAAAGTG |
| 577. | TGF-B2-N-21 | TTTTTTAAAAAAGTG |
| 578. | TGF-B2-N-22 | ATTTTTTAAAAAAGTG |
| 579. | TGF-B2-N-23 | CATTTTTTAAAAAAGT |
| 580. | TGF-B2-N-24 | GCATTTTTTAAAAAA |
| 581. | TGF-B2-N-25 | TGCATTTTTTAAAAAA |
| 582. | TGF-B2-N-26 | AGCTTATTTTAAAT |
| 583. | TGF-B2-N-27 | AAGCTTATTTTAAAT |
| 584. | TGF-B2-N-28 | TAAGCTTATTTTAAAT |
| 585. | TGF-B2-N-29 | TGTAATTATTAGAT |

FIG. 3-10

| | | |
|---|---|---|
| 586. | TGF-B2-N-30 | ATGTAATTATTAGAT |
| 587. | TGF-B2-N-31 | TGATGTAATTATTA |
| 588. | TGF-B2-N-32 | ATGATGTAATTATTA |
| 589. | TGF-B2-N-33 | ATGGTATTATATAA |
| 590. | TGF-B2-N-34 | TATGGTATTATATAA |
| 591. | TGF-B2-N-35 | TTATGGTATTATATAA |
| 592. | TGF-B2-N-36 | TTTATGGTATTATATAA |
| 593. | TGF-B2-N-37 | ATTTATGGTATTATATAA |
| 594. | TGF-B2-N-38 | AATCATATTAGAAA |
| 595. | TGF-B2-N-39 | TTACAATCATATTA |
| 596. | TGF-B2-N-40 | TTTACAATCATATTA |
| 597. | rb-1 | GGCATGACGCCTTTCC |
| 598. | rb-2 | GCATGACGCCTTTC |
| 599. | rb-3 | GCCTGACGAGAGGC |
| 600. | rb-4 | CTCAAGCCTGACGAG |
| 601. | rb-5 | CCACAGTTCCTTTTC |
| 602. | rb-6 | GCTGCAATAAAGATACAG |
| 603. | rb-7 | GCTGCAATAAAGATAC |
| 604. | rb-8 | GGACACTGATTTCTATG |
| 605. | rb-9 | GCATTATCAACTTTGG |
| 606. | rb-10 | ACTTTTAGCACCAATG |
| 607. | rb-11 | CCAAGAAACTTTTAGCACC |
| 608. | rb-12 | CCAGATCATCTTCC |
| 609. | rb-13 | AGTCAAGGACACATAG |
| 610. | rb-14 | TCTTTGAGCAACATGG |
| 611. | rb-15 | GGGTATAACAGCTG |
| 612. | rb-16 | GAGGTGAACCATTAATGG |
| 613. | rb-17 | TCTTCGTATCGTTTAG |
| 614. | rb-18 | TGTTGGATAGTGTTC |
| 615. | rb-19 | GTTGATCACTTGCTG |
| 616. | rb-20 | GGATTCCATTACTCG |
| 617. | rb-21 | GACATATGAAAAATGTTGTC |
| 618. | rb-22 | GCCAATAAAGACATATG |
| 619. | rb-23 | CCAGAATCAAGATTCTG |
| 620. | rb-24 | CTGTTCCAGAATCAAG |
| 621. | rb-25 | GACAAATCTGTTCCAGAATC |
| 622. | rb-26 | GGAAAGACAAATCTGTTCC |
| 623. | rb-27 | GATTAAGAGGACAAGC |
| 624. | rb-28 | GGAAGATTAAGAGG |
| 625. | rb-29 | GCAGTGTGATTATTCTGG |
| 626. | rb-30 | GGAGAAAGATACATATCTG |
| 627. | rb-31 | GGAGATCTTACAGG |
| 628. | rb-32 | GCATTTGCAGTAGAATTTAC |
| 629. | rb-33 | CAGTGAAAGAGAGG |
| 630. | rb-34 | GCTAGCCGATACAC |
| 631. | rb-35 | GGAAGATCCTTGTATGC |
| 632. | rb-36 | GCATGAGGAAGATCC |
| 633. | rb-37 | GGAGTCATTTTTGTTG |
| 634. | rb-38 | CCAATTGATACTAAGATTC |
| 635. | rb-39 | TCTTTTGAGCCACACG |
| 636. | rb-40 | CCTTCAGCACTTCTTTTG |
| 637. | rb-41 | GGTTGCTTCCTTCAGC |
| 638. | rb-42 | CAGTGGTTTAGGAG |
| 639. | rb-43 | CCTGAGATCCTCATTTC |
| 640. | rb-44 | CCAAGGTCCTGAGATCC |
| 641. | rb-45 | GGTGTACACAGTGTCC |
| 642. | rb-N-1 | TATCTTTAATTTCT |
| 643. | rb-N-2 | TCTTTTGAATATAA |
| 644. | rb-N-3 | TTCTTTTGAATATAA |
| 645. | rb-N-4 | TTTCTTTTGAATATAA |
| 646. | rb-N-5 | TTTTCTTTTGAATATAA |
| 647. | rb-N-6 | TTTTTCTTTTGAATATAA |
| 648. | rb-N-7 | ATTTCTATGTTTTT |
| 649. | rb-N-8 | TTAAAGAATTTATG |
| 650. | rb-N-9 | GTTAAAGAATTTAT |

FIG. 3-11

| | | |
|---|---|---|
| 651. | rb-N-10 | AGTTAAAGAATTTAT |
| 652. | rb-N-11 | AAGTTAAAGAATTTAT |
| 653. | rb-N-12 | TAAGTTAAAGAATTTAT |
| 654. | rb-N-13 | TTTAGTAAGTTAAA |
| 655. | rb-N-14 | TTTTAGTAAGTTAAA |
| 656. | rb-N-15 | ATTTCTTTTAGTAA |
| 657. | rb-N-16 | AATTTCTTTTAGTAA |
| 658. | rb-N-17 | ATCAATTTCTTTTA |
| 659. | rb-N-18 | TATCAATTTCTTTTA |
| 660. | rb-N-19 | AATATATAAGTTCA |
| 661. | rb-N-20 | AAATATATAAGTTCA |
| 662. | rb-N-21 | CAAATATATAAGTT |
| 663. | rb-N-22 | TCAAATATATAAGTT |
| 664. | rb-N-23 | TGTCAAATATATAA |
| 665. | rb-N-24 | AATTTATTTCAGTA |
| 666. | rb-N-25 | AATAAAAATGTGAT |
| 667. | rb-N-26 | TAATAAAAATGTGAT |
| 668. | rb-N-27 | TAGCTAATAAAAAT |
| 669. | rb-N-28 | TTAGCTAATAAAAAT |
| 670. | rb-N-29 | TTTAGCTAATAAAAAT |
| 671. | rb-N-30 | AATAAAATAGTCAA |
| 672. | rb-N-31 | TAATAAAATAGTCAA |
| 673. | rb-N-32 | TTAATAAAATAGTCAA |
| 674. | rb-N-33 | TTTAATAAAATAGTCAA |
| 675. | rb-N-34 | GTTTAATAAAATAGT |
| 676. | rb-N-35 | AGTTTAATAAAATAGT |
| 677. | rb-N-36 | GAGTTTAATAAAATA |
| 678. | rb-N-37 | AGAGTTTAATAAAATA |
| 679. | rb-N-38 | AATAATTCTTGTAT |
| 680. | rb-N-39 | TATATTACATTCAT |
| 681. | rb-N-40 | ATCTATATTACATT |
| 682. | rb-N-41 | ATAAACATTTTTCA |
| 683. | rb-N-42 | AATAAACATTTTTCA |
| 684. | rb-N-43 | AAATAAACATTTTTCA |
| 685. | rb-N-44 | GAAATAAACATTTTT |
| 686. | rb-N-45 | TGAAATAAACATTTTT |
| 687. | rb-N-46 | TTGAAATAAACATTTTT |
| 688. | rb-N-47 | TTTGAAATAAACATTTTT |
| 689. | rb-N-48 | TTTTGAAATAAACATTTTT |
| 690. | rb-N-49 | TTTTTGAAATAAACATTTT |
| 691. | rb-N-50 | ATTTTTGAAATAAACATTTT |
| 692. | rb-N-51 | AATTTTTGAAATAAACATT |
| 693. | rb-N-52 | AAATTTTTGAAATAAACATT |
| 694. | rb-N-53 | AAAATTTTTGAAATAAACAT |
| 695. | rb-N-54 | TAAAATTTTTGAAATAAACA |
| 696. | rb-N-55 | ATAAAATTTTTGAAATAAAC |
| 697. | rb-N-56 | TATAAAATTTTTGAAATAAA |
| 698. | rb-N-57 | GTATAAAATTTTTGAAAT |
| 699. | rb-N-58 | GGTATAAAATTTTT |
| 700. | rb-N-59 | AGGTATAAAATTTTT |
| 701. | rb-N-60 | AAGGTATAAAATTTTT |
| 702. | rb-N-61 | AAAGGTATAAAATTTTT |
| 703. | rb-N-62 | AAAAGGTATAAAATTTTT |
| 704. | rb-N-63 | TAAAAGGTATAAAATTTTT |
| 705. | rb-N-64 | ATAAAAGGTATAAAATTTTT |
| 706. | rb-N-65 | TTTAGAAAGATTTT |
| 707. | rb-N-66 | AAGATAAATTTCTT |
| 708. | rb-N-67 | TAAGATAAATTTCTT |
| 709. | rb-N-68 | TTAAGATAAATTTCTT |
| 710. | rb-N-69 | TTTAAGATAAATTTCTT |
| 711. | rb-N-70 | TTTTAAGATAAATTTCTT |
| 712. | rb-N-71 | TTTTTAAGATAAATTTCTT |
| 713. | rb-N-72 | ATTTTTAAGATAAATTTCTT |
| 714. | rb-N-73 | TATTTTTAAGATAAATTTCT |
| 715. | rb-N-74 | TTATTTTTAAGATAAATT |
| 716. | rb-N-75 | TTTATTTTTAAGATAAATT |
| 717. | rb-N-76 | CTTTATTTTTAAGATAAAT |

FIG. 3-12

| # | Name | Sequence |
|---|---|---|
| 718. | rb-N-77 | TCTTTATTTTTAAGATAAAT |
| 719. | rb-N-78 | ATCTTTATTTTTAAGATAAA |
| 720. | rb-N-79 | ATCTTTATTTTTAA |
| 721. | rb-N-80 | GATCTTTATTTTTAA |
| 722. | rb-N-81 | AGATCTTTATTTTTAA |
| 723. | rb-N-82 | TAGATCTTTATTTTTAA |
| 724. | rb-N-83 | AATCATCATTAATT |
| 725. | rb-N-84 | AAATCATCATTAATT |
| 726. | rb-N-85 | AAAATCATCATTAATT |
| 727. | rb-N-86 | TAAAATCATCATTAATT |
| 728. | rb-N-87 | TTAAAATCATCATTAATT |
| 729. | rb-N-88 | TTTAAAATCATCATTAATT |
| 730. | rb-N-89 | ATTTAAAATCATCATTAATT |
| 731. | rb-N-90 | AATTTAAAATCATCATTAA |
| 732. | rb-N-91 | GAATTTAAAATCAT |
| 733. | rb-N-92 | TGAATTTAAAATCAT |
| 734. | rb-N-93 | TTAAAATAGGAAAT |
| 735. | rb-N-94 | AATTTCTCTTTAAA |
| 736. | rb-N-95 | AAATTTCTCTTTAAA |
| 737. | rb-N-96 | TAAAATTTTGAATG |
| 738. | rb-N-97 | CTAAAATTTTGAAT |
| 739. | rb-N-98 | TTTGCTAAAATTTT |
| 740. | rb-N-99 | ATATGAAAAATGTT |
| 741. | rb-N-100 | TTTTAAATTAAGCA |
| 742. | rb-N-101 | TTGTAAAAATCAAA |
| 743. | rb-N-102 | TTTGTAAAAATCAAA |
| 744. | rb-N-103 | TTTGATAAAACTTT |
| 745. | rb-N-104 | ATGTTTTATCATTT |
| 746. | rb-N-105 | AATGTTTTATCATTT |
| 747. | rb-N-106 | AAATGTTTTATCATTT |
| 748. | rb-N-107 | TAAATGTTTTATCATTT |
| 749. | rb-N-108 | TCTAAATGTTTTAT |
| 750. | rb-N-109 | TTCTAAATGTTTTAT |
| 751. | rb-N-110 | TAAGATCAAATAAA |
| 752. | rb-N-111 | ATAAGATCAAATAAA |
| 753. | rb-N-112 | AATAAGATCAAATAAA |
| 754. | rb-N-113 | TAATAAGATCAAATAAA |
| 755. | rb-N-114 | TTAATAAGATCAAATAAA |
| 756. | rb-N-115 | TTTAATAAGATCAAATAAA |
| 757. | rb-N-116 | TTGTTTAATAAGAT |
| 758. | rb-N-117 | ATTGTTTAATAAGAT |
| 759. | rb-N-118 | TGATTGTTTAATAA |
| 760. | rb-N-119 | TTGATTGTTTAATAA |
| 761. | rb-N-120 | TTTGATTGTTTAATAA |
| 762. | rb-N-121 | TTTTATAAAACAGT |
| 763. | rb-N-122 | TTTTTATAAAACAGT |
| 764. | rb-N-123 | TTTTTTATAAAACAGT |
| 765. | rb-N-124 | CTTTTTTATAAAACA |
| 766. | rb-N-125 | ACTTTTTTATAAAACA |
| 767. | rb-N-126 | CACTTTTTTATAAAA |
| 768. | rb-N-127 | ACACTTTTTTATAAAA |
| 769. | rb-N-128 | TACACTTTTTTATAAAA |
| 770. | rb-N-129 | ATACACTTTTTTATAAAA |
| 771. | rb-N-130 | ATTTTGAATTTAAG |
| 772. | rb-N-131 | GATTTTGAATTTAA |
| 773. | rb-N-132 | TGATTTTGAATTTAA |
| 774. | rb-N-133 | ATGATTTTGAATTTAA |
| 775. | rb-N-134 | AATGATTTTGAATTTAA |
| 776. | rb-N-135 | ATAATAGAATCATA |
| 777. | rb-N-136 | TATAATAGAATCATA |
| 778. | rb-N-137 | TATAATAGAATCAT |
| 779. | rb-N-138 | TACTATAATAGAAT |
| 780. | rb-N-139 | ATACTATAATAGAAT |
| 781. | rb-N-140 | AATACTATAATAGAAT |
| 782. | rb-N-141 | AGAATACTATAATA |
| 783. | rb-N-142 | TAGAATACTATAATA |
| 784. | rb-N-143 | ATAGAATACTATAATA |

FIG. 3-13

| | | |
|---|---|---|
| 785. | rb-N-144 | TATAGAATACTATAATA |
| 786. | rb-N-145 | TTATAGAATACTATAATA |
| 787. | rb-N-146 | AATATTTGTTTTCA |
| 788. | rb-N-147 | AAATATTTGTTTTCA |
| 789. | rb-N-148 | AAAATATTTGTTTCA |
| 790. | rb-N-149 | CAAAATATTTGTTTT |
| 791. | rb-N-150 | AAATTTTATATGGA |
| 792. | rb-N-151 | TGAAATTTTATATG |
| 793. | rb-N-152 | CTGAAATTTTATAT |
| 794. | rb-N-153 | TCTGAAATTTTATAT |
| 795. | rb-N-154 | TTCTGAAATTTTATAT |
| 796. | rb-N-155 | ATCTGATTTATTTT |
| 797. | rb-N-156 | AAGATATTAAATGT |
| 798. | rb-N-157 | TGAAGATATTAAAT |
| 799. | rb-N-158 | ATAAATAACAATGA |
| 800. | rb-N-159 | TATAAATAACAATGA |
| 801. | rb-N-160 | GTATAAATAACAAT |
| 802. | rb-N-161 | TGTATAAATAACAAT |
| 803. | rb-N-162 | TTGTATAAATAACAAT |
| 804. | rb-N-163 | TCTTGTATAAATAA |
| 805. | rb-N-164 | ATCTTGTATAAATAA |
| 806. | rb-N-165 | ATTCTTGTATAAATAA |
| 807. | rb-N-166 | ACAACTTTTTAAAAT |
| 808. | rb-N-167 | TACAACTTTTTAAAT |
| 809. | rb-N-168 | TACAACTTTTTAAA |
| 810. | rb-T-1 | CGGGGGGTTTTGGGCGGCATG |
| 811. | rb-T-2 | TTTTCGGGGGGTTTTGGGCGGCA |
| 812. | rb-T-3 | TCGGGGGGTTTTGGGCGGC |
| 813. | rb-T-4 | GGTGGCGGCCGTTTTTCGGGGGGT |
| 814. | rb-T-5 | CCGGGGGTTCCGCGGCGGCAGCG |
| 815. | rb-T-6 | CGGGGGTTCCGCGGCGG |
| 816. | rb-T-7 | GGCGGGCGGTGCCGGGCGTTCCGC |
| 817. | rb-T-8 | GGAGGGGGCGGCGGCGGCGGTG |
| 818. | rb-T-9 | GGGGGCGGCGGCGGCGG |
| 819. | rb-T-10 | GGGGCGGCGGCGGCCG |
| 820. | rb-T-11 | AGGGGGCCTGGTGGAAG |
| 821. | rb-T-12 | TAGGGGGCCTGGTG |
| 822. | rb-T-13 | GTAGGGGGCCTGGT |
| 823. | rb-T-14 | GAGGTATTGGTGACAAGGTAGGGGGC |
| 824. | rb-T-15 | TCTTCAGGGGTGAAATATAGATGTTC |
| 825. | rb-T-16 | GGACTCTTCAGGGGTG |

FIG. 4-1

| | |
|---|---|
| 826 | TCGGACTATA CTGC |
| 827 | CAGTTCGGAC TATACT |
| 828 | AAGCCTAAGA CGCA |
| 829 | GCCCAAGTTC AACA |
| 830 | TGAAAAGTCG CGGT |
| 831 | GGTTAATTAA GATGCCTC |
| 832 | TCTCTAAGAG CGCA |
| 833 | ACGTGAGGTT AGTTG |
| 834 | CACGTGAGGT TAGT |
| 835 | CATAGAACAG TCCG |
| 836 | CAGTCATAGA ACAGTC |
| 837 | CTTTGCAGTC ATAGAACA |
| 838 | TGCAGTCATA GAAC |
| 839 | GGTCGTTTCC ATCT |
| 840 | CATAGAAGGT CGTTTC |
| 841 | CGTCATAGAA GGTC |
| 842 | CATCGTCATA GAAGG |
| 843 | GGACGGCAGG AACGAGGCGT TGAG |
| 844 | TAGCCATAAG GTCC |
| 845 | GGTTACTGTA GCCA |
| 846 | GGTTACTGTA GCCA |
| 847 | AGTTCTTGGC GCGGAGGT |
| 848 | AGGTGAGGAG GTCCGAGT |
| 849 | TGGACTGGAT TATCAG |
| 850 | GTGGTGGTGA TGTGCCCG |
| 851 | TGTCACGTTC TTGG |
| 852 | CTCATCTGTC ACGT |
| 853 | CGAAGCCCTC GGCGAACC |
| 854 | GCGTGTTCTG GCTGTGCAGT TCGG |
| 855 | CTGCCCCGTT GACC |
| 856 | AGGTTTGCGT AGAC |
| 857 | GGTTGAAGTT GCTG |
| 858 | CTGGGTTGAA GTTG |
| 859 | TGCTGCACGG GCATCTGCTG |
| 860 | GGCACTGTCT GAGGCTCCTC CTTCAGG |
| 861 | ACTCCATGTC GATG |
| 862 | CTCTCCGCCT TGATCC |
| 863 | GTTCCTCATG CGTTC |
| 864 | CTGAGCTTTC AAGG |
| 865 | GCGATTCTCT CCAGCTTCCT TTTTCG |
| 866 | CTGAGCTTTC AAGGTTTTCA CTTTTTCCTC |
| 867 | TCCCTGAGCA TGTT |
| 868 | TCTGTTTAAG CTGTGC |
| 869 | CTTTCTGTTT AAGCTGTG |
| 870 | GGTTCATGAC TTTCTG |
| 871 | CGTGGTTCAT GACT |
| 872 | ACTGTTAACG TGGTTC |
| 873 | CCACTGTTAA CGTG |
| 874 | CCCACTGTTA ACGT |
| 875 | AGCATGAGTT GGCA |
| 876 | GCGTTAGCAT GAGT |
| 877 | GTTTGCAACT GCTG |
| 878 | CAAAATGTTT GCAACTGC |

FIG. 4-2

| | |
|---|---|
| 879 | TCCATTTTAG TGCACATC |
| 880 | CTGTTCCATT TTAGTGCA |
| 881 | GTGTATGAGT CGTC |
| 882 | CTGTGTATGA GTCG |
| 883 | CGTAGCTGTG TATG |
| 884 | TCGTGTAGAG AGAG |
| 885 | AGTTTGTAGT CGTGTAGA |
| 886 | GTTTGTAGTC GTGTAG |
| 887 | AGTTTGTAGT CGTG |
| 888 | GGAGTTTGTA GTCG |
| 889 | TCAGGAGTTT GTAGTC |
| 890 | GTTTCAGGAG TTTGTAGT |
| 891 | TCGGTTTCAG GAGT |
| 892 | TTGAGACTCC GGTA |
| 893 | ACCAGAAAAG TAGCTG |
| 894 | CCTGACCAGA AAAG |
| 895 | ATTCAGGCGT TCCA |
| 896 | GGTAAAAGTA CTGTCC |
| 897 | GGGTAAAAGT ACTGTC |
| 898 | GCACCTCCAC CGCTGCCA |
| 899 | CTCCTGCTCC TCGGTGAC |
| 900 | GCTTTGACAA AGCC |
| 901 | CTTGTGCAGA TCGT |
| 902 | TCATCTTGTG CAGATC |
| 903 | GTTCATCTTG TGCAGA |
| 904 | CGTGGTTCAT CTTG |
| 905 | TCACGTGGTT CATC |
| 906 | GGTTGGTGTA AACG |
| 907 | TACGAGCTCC CGGTCCCGAC |
| 908 | TAGCTGATGG TGGT |
| 909 | TCCTTGAAGG TGGA |
| 910 | TCTTCCATGT TGATGG |
| 911 | CTTTGATGCG CTCT |
| 912 | CTCCACTTTG ATGC |
| 913 | GCTCCAGCTT CCGCTTCCGG CACTTGGTGG |
| 914 | GGCCTTGAGC GTCTTCACCT TGTCCTCCAG |
| 915 | TGACCTTCTG TTTGAG |
| 916 | CATGACCTTC TGTTTG |
| 917 | GTCATGACCT TCTG |
| 918 | CGAGAACATC ATCG |
| 919 | GTAGTCTGCG TTGA |
| 920 | GCTGCAGCGG GAGGATGACG |
| 921 | AGTAAGAGAG GCTATC |
| 922 | GTAGTAAGAG AGGC |
| 923 | GGTAGTAAGA GAGG |
| 924 | GTGAGTGGTA GTAAGA |
| 925 | GTCCGTGCAG AAGTCCTG |
| 926 | GAATGAAGTT GGCACT |
| 927 | GGAATGAAGT TGGC |
| 928 | GGGAATGAAG TTGG |
| 929 | GCTGCACCAG CCACTGCAGG TCCGGACTGG |
| 930 | TCATGGTCTT CACAAC |
| 931 | CAATGCTCTG CGCTCGGCCT CCTGTCATGG |

FIG. 4-3

| | |
|---|---|
| 932 | CTAGAGTTCC TCAC |
| 933 | GAGTACGCTA GAGT |
| 934 | GAAGAGTACG CTAG |
| 935 | CTGCTTCCCA CCCAGCCCCC ACATTCCC |
| 936 | TTCATCCTCT GTACTGGGCT |
| 937 | GTTACGGATG TGCA |
| 938 | CAGTTACGGA TGTG |
| 939 | CCAGTTACGG ATGT |
| 940 | AGAGGTCTGAG TTGG |
| 941 | GTGAGACTCA GAGT |
| 942 | TCTTAGGGTG AGAC |
| 943 | GAGAGTACTT CTTAGG |
| 944 | GGAAGAAACT ATGAGAGT |
| 945 | CTTAGGGAAG AAACTATG |
| 946 | CGGTAAGAAA CTTAGG |
| 947 | AGCATGCGGT AAGA |
| 948 | GTCTGAAAGC ATGC |
| 949 | AGAACAAAGA AGAGCC |
| 950 | CAAGAGAACA AAGAAGAG |
| 951 | CAGCAAGAGA ACAAAG |
| 952 | TCCTCAGCAA GAGA |
| 953 | AGGTGTGACT TGCA |
| 954 | GAATAGGTGT GACTTG |
| 955 | CAGAATAGGT GTGACT |
| 956 | GCAGAATAGG TGTG |
| 957 | CAGTTGCAGA ATAGGT |
| 958 | GAAACCATTT CTGACC |
| 959 | TGTGAAACCA TTTCTGAC |
| 960 | CACTGTGAAA CCATTTCT |
| 961 | CCACTGTGAA ACCA |
| 962 | AGAACTGGCT CCTGCAGCTT CCCTGCTTCC |
| 963 | CACCTCCATT CACCC |
| 964 | CAGTAAAAGT GTCTGC |
| 965 | CGACATTCAG TAAAAGTG |
| 966 | GACCGACATT CAGT |
| 967 | CTTCTGGAGA TAACTAGA |
| 968 | CATCTTATTC CTTTCCCT |
| 969 | CAGCCATCTT ATTCCT |
| 970 | TGCAGCCATC TTATTC |
| 971 | GAGTGTATCA GTCAG |
| 972 | GGAGTGTATC AGTC |
| 973 | CTTGGAGTGT ATCAGT |
| 974 | ACAGAGTACC TACC |
| 975 | CCAACTTTCC CTTAAG |
| 976 | CCTTATGCTC AATCTC |
| 977 | GTCTTACTCA AGGG |
| 978 | ACAGTCTTAC TCAAGG |
| 979 | CATAAGACAC AGTCTTAC |
| 980 | GAAAGCATAA GACACAGT |
| 981 | GGAAAGCATA AGACAC |
| 982 | AGGGATAAAG GAAAGC |
| 983 | CCTGTATACA GAGG |
| 984 | TGTCTCCTGT ATACAG |

FIG. 4-4

| | |
|---|---|
| 985 | CATCTTCTAG TTGGTC |
| 986 | CTCATCTTCT AGTTGG |
| 987 | CTTCTCATCT TCTAGTTG |
| 988 | CAAAAGCAGAC TTCTCA |
| 989 | CTGCAAAGCA GACT |
| 990 | CTAGTTTTTC CTTCTCCT |
| 991 | TCTAGTTTTT CCTTCTCC |
| 992 | CAGGATGAAC TCTAGT |
| 993 | TCGTAGAAGG TCGT |
| 994 | AGGGTTACTG TAGC |
| 995 | GTAGTGGTGA TGTG |
| 996 | CGTCGTAGAA GGTC |
| 997 | TTTCGTGCAC ATCC |
| 998 | AGTTTGTAGT CGTGAAGA |
| 999 | CGAGAACATC ATGG |
| 1000 | GTAGTAGGAA ACGC |
| 1001 | GGTAGTAGGA AAGG |
| 1002 | GGAATGGTAG TAGG |
| 1003 | GGTCATTGAG AAGAG |
| 1004 | GCTAATGTTC TTGACC |
| 1005 | GCCAAGGTCCTCAT |
| 1006 | GGAGTCTATCTCCA |
| 1007 | CCAAAGAATCCTGACT |
| 1008 | CACATGCTTAGTGG |
| 1009 | CTCGTAAATGACCG |
| 1010 | AGGAATCTCGTAAATGAC |
| 1011 | CAGCAGCGATTCAT |
| 1012 | GGAGATCATCAAAGGA |
| 1013 | CTCAGCAATGGTCA |
| 1014 | GATCTCGAACACCT |
| 1015 | CACAATCTCGATCTTTCT |
| 1016 | CCTTCTTAAAGATTGGCT |
| 1017 | CACATACCAACTGG |
| 1018 | AGCTTGATGTGAGG |
| 1019 | GAAGTTGTAGCTTGATGT |
| 1020 | GCTTGAAGTTGTAGCT |
| 1021 | CTGCTTGAAGTTGTAG |
| 1022 | GACACAACTCCTCT |
| 1023 | TCCTTTGATAGACACAAC |
| 1024 | CTCGTTTGATAGACAC |
| 1025 | GGTTAGCACACACT |
| 1026 | GGTAACGGTTAGCA |
| 1027 | CGTAACACATTTAGAAGC |
| 1028 | CTCATCCGTAACAC |
| 1029 | CCGGTAAGTATTGTAGTT |
| 1030 | GGTGTATTTCCTTGAC |
| 1031 | ACATACCAACTGGTGT |
| 1032 | GTCCCTATACGAAC |
| 1033 | TTCATGTCTG TGCC |
| 1034 | GTAGGTGAGT TCCA |
| 1035 | GTTGTGAGCG ATGA |
| 1036 | CATAGTTGTC CTCAAAGA |
| 1037 | GGCATAGTTG TCCT |

FIG. 4-5

| | |
|---|---|
| 1038 | CATTGTCTAG CACG |
| 1039 | CTCCATTGTC TAGC |
| 1040 | GTATTGTTCA GCGG |
| 1041 | TACCGATCTC TGTGAG |
| 1042 | CACAAAATCG TGTCCT |
| 1043 | TCCTTCCACA AAATCG |
| 1044 | GTGGAAGATG TCCT |
| 1045 | TCTTGTGGAA GATGTC |
| 1046 | TCTATCAGTG TGAGAG |
| 1047 | GGTTGGTGTC TATC |
| 1048 | ACATCGGAGA ACAG |
| 1049 | CCTTACACAT CGGA |
| 1050 | ACAATCCTCA GAACTC |
| 1051 | GCTCTGACAA TCCT |
| 1052 | TGGTTGAAGT GGAG |
| 1053 | CTGTGGTTGA AGTG |
| 1054 | GTTGTAGGTG ACCA |
| 1055 | CTGTGTTGTA GGTG |
| 1056 | GACTCAAACG TGTC |
| 1057 | CATGGACTCA AACG |
| 1058 | CGAATGTATA CCGG |
| 1059 | CCGAATGTAT ACCG |
| 1060 | GCCGAATGTA TACC |
| 1061 | GTAGTTGTAG GGAC |
| 1062 | TAGAAAGGTA GTTGTAGG |
| 1063 | GTAGAAAGGT AGTTGTAG |
| 1064 | CGTAGAAAGG TAGTTG |
| 1065 | CCGTAGAAAG GTAG |
| 1066 | GACCATAGCA CACT |
| 1067 | GGATATTGGC ACTG |
| 1068 | CCTGGATATT GGCA |
| 1069 | GCTCCCAAAG ATCT |
| 1070 | CCCATCAAAG CTCT |
| 1071 | CAAACACTTG GAGC |
| 1072 | GTCTCAAACA CTTGGA |
| 1073 | GAGTCTCAAA CACTTG |
| 1074 | GTAACCTGTG ATCTCT |
| 1075 | GGTAACCTGT GATC |
| 1076 | GTATAGGTAA CCTGTG |
| 1077 | TGAGATGTAT AGGTAACC |
| 1078 | TGCTGAGATG TATAGG |
| 1079 | CCATGCTGAG ATGT |
| 1080 | GGATTACTTG CAGG |
| 1081 | TGTTATGGTG GATGAG |
| 1082 | GGTGTTATGG TGGA |
| 1083 | GCAGTTGACA CACT |
| 1084 | AGTACTCGGC ATTC |
| 1085 | CATTCACATA CTCCCT |
| 1086 | TCCAAAACAG GTCACT |
| 1087 | GGTCCTTATA GTGG |
| 1088 | CAGAATGCCA ACCA |
| 1089 | ACGAGAATGC CAAC |
| 1090 | GATCCCAAAG ACCA |

FIG. 4-6

| | |
|---|---|
| 1091 | TCGCTTGATG AGGA |
| 1092 | CATCGTGTAC TTCC |
| 1093 | GCATCGTGTA CTTC |
| 1094 | ACTGTGCCAA AAGC |
| 1095 | CTTGTAGACT GTGC |
| 1096 | CCCTTGTAGA CTGT |
| 1097 | TCAACACTTT GATGGC |
| 1098 | CCCTCAACAC TTTG |
| 1099 | GTGTTTTCCC TCAACA |
| 1100 | GTATGCTTCG TCTAAG |
| 1101 | CGTATGCTTC GTCT |
| 1102 | CCATCACGTA TGCT |
| 1103 | GCATAAGCTG TGTC |
| 1104 | CATGGTCTAA GAGG |
| 1105 | CAATCTGCAT ACACCA |
| 1106 | GGCAATCTGC ATAC |
| 1107 | CTGTCTCGTC AATG |
| 1108 | CATAACTCCA CACATC |
| 1109 | AGTCACACCA TAACTC |
| 1110 | ACAGTCACAC CATAAC |
| 1111 | CCCCAAAAGT CATC |
| 1112 | TCGTTAAGGTT TGGC |
| 1113 | GATCCCATCG TAAG |
| 1114 | CAATGGTGCA GATG |
| 1115 | GACATCAATG GTGC |
| 1116 | GTAGACATCA ATGGTG |
| 1117 | CATGATCATG TAGACATC |
| 1118 | CCATGATCAT GTAGAC |
| 1119 | CATTTGACCA TGATCATG |
| 1120 | CCAACATTTG ACCATG |
| 1121 | TCATCCAACA TTTGACCA |
| 1122 | GAGTCAATCA TCCAACAT |
| 1123 | CAGAGTCAAT CATCCA |
| 1124 | CCGACATTCA GAGT |
| 1125 | GAATTCAGAC ACCAAC |
| 1126 | GATGACCACA AAGC |
| 1127 | CCATCAAATA CATCGG |
| 1128 | TCACCATCAA ATACATCG |
| 1129 | CAACGTAGCC ATCA |
| 1130 | ACGTCTTTGA CGAC |
| 1131 | CAAAAACGTC TTTGACGA |
| 1132 | GGCAAAAACG TCTTTG |
| 1133 | CAAAGGCAAA AACGTC |
| 1134 | GTGTCAAGTA CTCG |
| 1135 | GTAATAGAGG TTGTCG |
| 1136 | CCCAGTAATA GAGG |
| 1137 | CATGGTGCTC ACTG |
| 1138 | GTGCCTGTAC GTAC |
| 1139 | TGCAGGTGGA TAGT |
| 1140 | CATGTCGATA GTCTTGCA |
| 1141 | GTCGATAGTC TTGC |
| 1142 | CCATGTCGAT AGTC |
| 1143 | CTCCATGTCG ATAG |

FIG. 4-7

| | |
|---|---|
| 1144 | CTTGGACAGG ATCT |
| 1145 | TGCTGTTGTA CAGG |
| 1146 | GTGCTGTTGT ACAG |
| 1147 | TTGGCGTAGT AGTC |
| 1148 | TCCACCATTA GCAC |
| 1149 | GATTTCGTTG TGGG |
| 1150 | GTCATAGATT TCGTTGTG |
| 1151 | TGTACTCTGC TTGAAC |
| 1152 | GTGTACTCTG CTTG |
| 1153 | TGCTGTGTGT ACTC |
| 1154 | CTGATGTGTT GAAGAACA |
| 1155 | CTCTGATGTG TTGAAG |
| 1156 | GCTCTGATGT GTTG |
| 1157 | GAGCTCTGAT GTGT |
| 1158 | CACTTTTAAC TTGAGCCT |
| 1159 | CTCCACTTTT AACTTGAG |
| 1160 | TGCTGTATTT CTGGTACA |
| 1161 | CCAGGAATTG TTGC |
| 1162 | TTGCTGAGGT ATCG |
| 1163 | GATAACCACT CTGG |
| 1164 | CAAAAGATAA CCACTCTG |
| 1165 | CGGTGACATC AAAAG |
| 1166 | CCTCAATTTC CCCT |
| 1167 | GTTATCCCTG CTGT |
| 1168 | GCAGTGTGTT ATCC |
| 1169 | GATGTCCACT TGCA |
| 1170 | TAGTGAACCC GTTG |
| 1171 | TGCCATGAAT GGTG |
| 1172 | GTTCATGCCA TGAATG |
| 1173 | CATGAGAAGC AGGA |
| 1174 | GCTTTGCAGA TGCT |
| 1175 | GAGCTTTGCA GATG |
| 1176 | TAGTTGGTGT CCAG |
| 1177 | CTGAAGCAAT AGTTGG |
| 1178 | AGCTGAAGCA ATAGTTGG |
| 1179 | GGAGCTGAAG CAAT |
| 1180 | CAATGTACAG CTGC |
| 1181 | GGAAGTCAAT GTACAG |
| 1182 | GGAAGTCAAT GTACAG |
| 1182 | CGGAAGTCAA TGTAC |
| 1183 | GCGGAAGTCA ATGT |
| 1184 | AGTTGGCATG GTAG |
| 1185 | GCAGAAGTTG GCAT |
| 1186 | CTCCAAATGT AGGG |
| 1187 | ACCTTGCTGT ACTG |
| 1188 | TGCTGGTTGT ACAG |
| 1189 | GGTTATGCTG GTTG |
| 1190 | GTAGTACACG ATGG |
| 1191 | CGTAGTACAC GATG |
| 1192 | CACGTAGTAC ACGA |
| 1193 | CATGTTGGAC AGCT |
| 1194 | GCACGATCAT GTTG |
| 1195 | CACACAGTAG TGCA |
| 1196 | GATCAGAAAA GCGC |

FIG. 4-8

```
1197  ACCGTGACCA GATG
1198  GTAGACAGGC TGAG
1199  TATCGAGTGT GCTG
1200  TTGCGCATGA ACTG
1201  TTGCTCAGGA TCTG
1202  ACTGGTGAGC TTCA
1203  GCTCAGGATA GTCT
1204  TGTAGATGGA AATCACCT
1205  TGGTGCTGTT GTAG
1206  TTCTCCTGGA GCAA
1207  TACTCTTCGT CGCT
1208  CTTGGCGTAG TACT
1209  CGGCATGTCT ATTTTGTA
1210  CGGGATGGCA TTTT
1211  CTGTAGAAAG TGGG
1212  ACAATTCTGA AGTAGGGT
1213  ATTGCTGAGA CGTCAAAT
1214  TCTCCATTGC TGAG
1215  TCACCAAATT GGAAGCAT
1216  CTCTGAACTC TGCT
1217  AACGAAAGAC TCTGAACT
1218  TGGGTTCTGC AAAC
1219  CTGGCTTTTG GGTT
1220  GTTGTTCAGG CACT
1221  TCTGATATAG CTCAATCC
1222  TCTTTGGACT TGAGAATC
1223  TGGGTTGGAG ATGT
1224  TGCTGTCGAT GTAG
1225  ACAACTTTGC TGTCGA
1226  ATTCGCCTTC TGCT
1227  GAAGGAGAGC CATT
1228  TCAGTTACAT CGAAGG
1229  TGAAGCCATT CATGAACA
1230  TCCTGTCTTT ATGGTG
1231  AAATCCCAGG TTCC
1232  GGACAGTGTA AGCTTATT
1233  GTACAAAAGT GCAGCA
1234  TAGATGGTAC AAAAGTGC
1235  CACTTTTATT TGGGATGATG
1236  GCAAATCTTG CTTCTAGT
1237  GTGCCATCAA TACC
1238  GGTATATGTG GAGG
1239  TCTGATCACC ACTG
1240  TCCTAGTGGA CTTTATAG
1241  TTTTTCCTAG TGGACT
1242  CAATAACATT AGCAGG
1243  AAGTCTGTAG GAGG
1244  TCTGTTGTGA CTCAAG
1245  GTTGGTCTGT TGTG
1246  CAAAGCACGC TTCT
1247  TTTCTAAAGC AATAGGCC
1248  GCAATTATCC TGCACA
1249  ACGTAGGCAG CAAT
```

FIG. 4-9

| | |
|---|---|
| 1250 | ATCAATGTAA AGTGGACG |
| 1251 | CTAGATCCCT CTTG |
| 1252 | CCATTTCCAC CCTA |
| 1253 | TGGGTTCGTG TATC |
| 1254 | TGGCATTGTA CCCT |
| 1255 | TCCAGCACAG AAGT |
| 1256 | ATAAATACGG GCATGC |
| 1257 | AGTGTCTGAA CTCC |
| 1258 | TGTGCTGAGT GTCT |
| 1259 | ATAAGCTCAG GACC |
| 1260 | AGGAGAAGCA GATG |
| 1261 | AGCAAGGAGA AGCA |
| 1262 | AATCTTGGGA CACG |
| 1263 | TAGAGAATGG TTAGAGGT |
| 1264 | GTTTTGCCAA TGTAGTAG |
| 1265 | CTTGGGTGTT TTGC |
| 1266 | GCAAGACTTT ACAATC |
| 1267 | GCATTTGCAA GACTTTAC |
| 1268 | TTTAGCTGCA TTTGCAAG |
| 1269 | GCCACTTTTC CAAG |
| 1270 | TTGGTCTTGC CACT |
| 1271 | CAGCACACAG TAGT |
| 1272 | CGATAGTCTT GCAG |

FIG. 5-1

| | | |
|---|---|---|
| 1273 | TGF-B2-14/1 | CTTTCACCAAATTGGAAG |
| 1274 | TGF-B2-14/2 | CACCAAATTGGAAGC |
| 1275 | TGF-B2-14/3 | TCACCAAATTGGAAGC |
| 1276 | TGF-B2-14/4 | CTCTGGCTTTTGGG |
| 1277 | TGF-B2-14/5 | CGGCATGTCTATTTG |
| 1278 | relA-1 | CACTACAGACGAGC |
| 1279 | relA-2 | CGTGCACTACAGACG |
| 1280 | relA-3 | GGAACAGTTCGTCC |
| 1281 | relA-4 | GAACAGTTCGTCCATG |
| 1282 | relA-5 | CCAGAGTTTCGGTTC |
| 1283 | relA-6 | CTAGGACTGGGACAG |
| 1284 | relA-7 | CGCACTTGTAGCG |
| 1285 | relA-8 | CTCGCACTTGTAGC |
| 1286 | relA-9 | GCACTTGTAGC |
| 1287 | relA-10 | GCGCACTGTCCCTG |
| 1288 | relA-11 | CCAGGGAGATGCGC |
| 1289 | relA-12 | GCCGGTGAGGAGG |
| 1290 | relA-13 | CCGGTGAGGAGGG |
| 1291 | relA-14 | CGGTTCACTCGGC |
| 1292 | relA-15 | GAGTTTCGGTTCACTC |
| 1293 | relA-16 | GGCACGATTGTCAAAG |
| 1294 | relA-17 | CAGGCGTCACCCCC |
| 1295 | relA-18 | GCAGGCGTCACCC |
| 1296 | p105/p50-1 | CTCCCTCCTAAGC |
| 1297 | p105/p50-2 | CCCTCCTAAGCGG |
| 1298 | p105/p50-3 | CGAGTCCGCGTTCG |
| 1299 | p105/p50-4 | CATCTTCTGCCATTC |
| 1300 | p105/p50-5 | GTGTTTTCCCACCAG |
| 1301 | p105/p50-6 | GGTTTTGGTTCACTAC |
| 1302 | p105/p50-7 | GCATCTTCACGTCTCC |
| 1303 | p105/p50-8 | CTTCACGTCTCCTGTC |
| 1304 | p105/p50-9 | GTCACCGCGTAGTC |
| 1305 | p105/p50-10 | CAAATAGGCAAGGTC |
| 1306 | p105/p50-11 | CTTGCAAATAGGCAAG |
| 1307 | p105/p50-12 | TGCTTGCAAATAGG |
| 1308 | p105/p50-13 | CTGCTTGCAAATAGG |
| 1309 | p105/p50-14 | GCAGGTGGATATTT |
| 1310 | p105/p50-15 | CTGCTGTTGGCAG |
| 1311 | p105/p50-16 | CACTAGTTTCCAAGT |
| 1312 | p105/p50-17 | GTTTTGGTTCACTAG |
| 1313 | p105/p50-18 | CTTTGATTTCAGGATAG |

FIG. 5-2

| | | |
|---|---|---|
| 1314 | p105/p50-19 | GCACTTCTTCTTTATCT |
| 1315 | p105/p50-20 | CCAAGTCAGATTTCC |
| 1316 | p105/p50-21 | GTTTCCAAGTCAGATTTC |
| 1317 | p105/p50-22 | GGTTCACTAGTTTCC |
| 1318 | p105/p50-23 | GGTTTTGGTTCACTAG |
| 1319 | p105/p50-24 | CCGAAAAATTGGGCA |
| 1320 | p105/p50-25 | CCGAAAAATTGGG |
| 1321 | p105/p50-26 | CTATCCGAAAAATTGG |
| 1322 | p105/p50-27 | GTTGATAATGTCATCAG |
| 1323 | p105/p50-28 | CTCATGTTGATAATGTC |
| 1324 | p105/p50-29 | CTGTCACCGCGTAG |
| 1325 | p105/p50-30 | CGTCTCCTGTCACCG |
| 1326 | p105/p50-31 | CTTCACGTCTCCTG |
| 1327 | p105/p50-32 | GAGAACTTTATCATGTC |
| 1328 | p105/p50-33 | GCTATATGCAGGG |
| 1329 | p105/p50-34 | CCAGCTGCTATATGCAGG |
| 1330 | p105/p50-35 | AGGCTAAATTTTGCCT |
| 1331 | p105/p50-36 | GGCTAAATTTTGCC |
| 1332 | p105/p50-37 | GGCTAAATTTTGCCTTC |
| 1333 | p105/p50-38 | GCAGGCTAAATTTTGCC |
| 1334 | p105/p50-39 | GAGTTACCCAAGCG |
| 1335 | p105/p50-40 | CAGAGTTACCCAAGCG |
| 1336 | p105/p50-41 | CAGAGTTACCCAAG |
| 1337 | p105/p50-42 | ACAGAGTTACCCAAG |
| 1338 | p105/p50-43 | GGTGCAAAACAGAG |
| 1339 | p105/p50-44 | CTAGGTGCAAAACAG |
| 1340 | p105/p50-45 | GAGAACTTTATCATGTCC |
| 1341 | p105/p50-46 | GCTAGATGAATGGC |
| 1342 | p105/p50-47 | GCAAACATGGCAGGC |
| 1343 | p105/p50-48 | CAGCAAACATGGCA |
| 1344 | p105/p50-49 | GCAGCAAACATGGC |
| 1345 | p105/p50-50 | AGCAGCAAACATGG |
| 1346 | p105/p50-51 | CAGCAGCAAACATG |
| 1347 | p105/p50-52 | AGCAGCAGCAAACA |
| 1348 | p105/p50-53 | CAGCAGCAGCAAACA |
| 1349 | p105/p50-54 | CAGCAGCAGCAAAC |
| 1350 | p105/p50-55 | CACCAGCAGCAGCA |
| 1351 | p105/p50-56 | GCATTGACGTCAGC |
| 1352 | p105/p50-57 | GATGTTGTCGTGCTC |
| 1353 | p105/p50-58 | TGAGATGTTGTCGTGCT |
| 1354 | p105/p50-59 | TGAGATGTTGTCGTG |

FIG. 5-3

| | | |
|---|---|---|
| 1355 | p105/p50-60 | GCCAATGAGATGTTG |
| 1356 | p105/p50-61 | CTGCCAATGAGATG |
| 1357 | p105/p50-62 | CACATGGGCATCAC |
| 1358 | p105/p50-63 | TGTCCACATGGGCA |
| 1359 | p105/p50-64 | GTACTGTCCACATG |
| 1360 | p105/p50-65 | CAGCTGCTATATGC |
| 1361 | p105/p50-66 | GTTCTCCACCAGGG |
| 1362 | p105/p50-67 | AGTTCTCCACCAGG |
| 1363 | p105/p50-68 | CAAAGTTCTCCACCAG |
| 1364 | p105/p50-69 | CCAAGAGTCATCCAGG |
| 1365 | p105/p50-70 | CCCAAGAGTCATCC |
| 1366 | p105/p50-71 | CCTGCATTTTCCCAAG |
| 1367 | p105/p50-72 | TCCTGCATTTTCCC |
| 1368 | p105/p50-73 | GCCATATCTAGAGGC |
| 1369 | p105/p50-74 | TCACATCTTCAGCC |
| 1370 | p105/p50-75 | GCTTCACATCTTCAGC |
| 1371 | p105/p50-76 | CAGCTTCACATCTTC |
| 1372 | p105/p50-77 | GTAACTTATACAGCTGC |
| 1373 | p105/p50-78 | CCAGTTTTTGTCTGG |
| 1374 | p105/p50-79 | CCATTTGTCTCAGG |
| 1375 | p105/p50-80 | GTGTAGCCCATTTG |
| 1376 | p105/p50-81 | GCTTCGGTGTAGCC |
| 1377 | p105/p50-82 | GATCACTTCAATTGCTTC |
| 1378 | p105/p50-83 | CTTGTGGAGGCAGG |
| 1379 | p105/p50-84 | GCTGCCTTGTGGAG |
| 1380 | p105/p50-85 | CTATTTGCTGCCTTGTGG |
| 1381 | p105/p50-86 | GGATGTCTCCACGC |
| 1382 | p105/p50-87 | CGAAGGATGTCTCC |
| 1383 | p105/p50-88 | TGCGGAAGGATGTC |
| 1384 | p105/p50-89 | GTTTGCGGAAGGATGTC |
| 1385 | p105/p50-90 | GCTGAGTTTGCGGA |
| 1386 | p105/p50-91 | GGTAAAGCTGAGTTTG |
| 1387 | p105/p50-92 | TCGGTAAAGCTGAG |
| 1388 | p105/p50-93 | GACTCGGTAAAGCTG |
| 1389 | p105/p50-94 | AGAGACTCGGTAAAGC |
| 1390 | p105/p50-95 | GAAATTGTCAGCAGGC |
| 1391 | p105/p50-96 | GAAATTGTCAGCAGG |
| 1392 | p105/p50-97 | GGAAATTGTCAGCAGG |
| 1393 | p105/p50-98 | GGAAATTGTCAGCAG |
| 1394 | p105/p50-99 | GGGAAATTGTCAGC |
| 1395 | p105/p50-100 | GTGTGGGAAATTGTC |

FIG. 5-4

| | | |
|---|---|---|
| 1396 | p105/p50-101 | GGTTTACACGGTGTG |
| 1397 | p105/p50-102 | GCTTTGGTTTACACG |
| 1398 | p105/p50-103 | GCACCTTTGGGATGC |
| 1399 | NFKB2-1 | CCAGGTTCTGCTTCC |
| 1400 | NFKB2-2 | GCTCTGTCTAGTGGC |
| 1401 | NFKB2-3 | ACTCTCCATGTCTC |
| 1402 | NFKB2-4 | CAACTCTCCATGTCTC |
| 1403 | NFKB2-5 | CAACTCTCCATGTC |
| 1404 | NFKB2-6 | AGCAACTCTCCATG |
| 1405 | NFKB2-7 | GTAGCAACTCTCCATG |
| 1406 | NFKB2-8 | GTAGCAACTCTCCA |
| 1407 | NFKB2-9 | GGTTGTAGCAACTCTCC |
| 1408 | NFKB2-10 | CGGGCAGTCCTCCA |
| 1409 | NFKB2-11 | GCACCGGGCAGTC |
| 1410 | NFKB2-12 | AGGCACCGGGCAG |
| 1411 | NFKB2-13 | GTGTGTTACCAGGTC |
| 1412 | NFKB2-14 | TGTGTGTTACCAGGT |
| 1413 | NFKB2-15 | TGGGTCACTGTGTG |
| 1414 | NFKB2-16 | CAGACTGTGGGCATG |
| 1415 | NFKB2-17 | CCCACCAGACTGTGGG |
| 1416 | NFKB2-18 | CCACCAGACTGTGG |
| 1417 | NFKB2-19 | TGCCCACCAGACTG |
| 1418 | NFKB2-20 | CGGCTTCCTCCCC |
| 1419 | NFKB2-21 | CCTTGTCTTCCACC |
| 1420 | NFKB2-22 | ACCGAGGCTGCCAC |
| 1421 | NFKB2-23 | GGAAGAAACCGAGG |
| 1422 | NFKB2-24 | GGGAAGAAACCGAG |
| 1423 | NFKB2-25 | GGCCATCTGCGCC |
| 1424 | NFKB2-26 | GCGGCCATCTGCG |
| 1425 | NFKB2-27 | GTGGCGGCCATCTG |
| 1426 | NFKB2-28 | ACCGTGGCGGCCAT |
| 1427 | NFKB2-29 | GCCGCTCAATCTTCATC |
| 1428 | NFKB2-30 | CTTCATCTTGTGATAGG |
| 1429 | NFKB2-31 | GCTCAATCTTCATCTTG |
| 1430 | NFKB2-32 | CAGAAACACTGTTACAG |
| 1431 | NFKB2-33 | CAGTTGCAGAAACACTG |
| 1432 | NFKB2-34 | GTTTCAGTTGCAGAAAC |
| 1433 | NFKB2-35 | CTTCCACCAGAGGG |
| 1434 | NFKB2-36 | GTCTTCCACCAGAG |
| 1435 | NFKB2-37 | CTTGTCTTCCACCAGAG |
| 1436 | NFKB2-38 | TCCTTGTCTTCCAC |

FIG. 5-5

| | | |
|---|---|---|
| 1437 | NFKB2-39 | CTTCCTTGTCTTCCAC |
| 1438 | NFKB2-40 | CATCTTGTGATAGGG |
| 1439 | NFKB2-41 | GCTAGGTGCAGTGGT |
| 1440 | NFKB2-42 | GATGGCTAGGTGCA |
| 1441 | NFKB2-43 | GTGGATGATGGCTAG |
| 1442 | NFKB2-44 | CCCGTGGATGATGG |
| 1443 | NFKB2-45 | CTGCCCGTGGATGA |
| 1444 | NFKB2-46 | AGAGCCTCCACCCA |
| 1445 | NFKB2-47 | GTTGTACTCTCGAGC |
| 1446 | NFKB2-48 | CGTTGTACTCTCG |
| 1447 | NFKB2-49 | CGCGTTGTACTCTC |
| 1448 | NFKB2-50 | GAGTCTCCATGCCG |
| 1449 | NFKB2-51 | CTGAGTCTCCATGC |
| 1450 | NFKB2-52 | CATGGCTGAGTCTC |
| 1451 | NFKB2-53 | TGCATGGCTGAGTC |
| 1452 | NFKB2-54 | GCGTTCACGTTGGC |
| 1453 | NFKB2-55 | GTGCGAGCGTTCAC |
| 1454 | NFKB2-56 | AGGTGCGAGCGTTC |
| 1455 | NFKB2-57 | GCAAAGGTGCGAGC |
| 1456 | NFKB2-58 | CCTGGTGGCTCAGG |
| 1457 | NFKB2-59 | GTCAGTCACCTGAG |
| 1458 | NFKB2-60 | CAGGTCAGTCACCTG |
| 1459 | NFKB2-61 | CAGCAGGTCAGTCAC |
| 1460 | NFKB2-62 | GCAGCAGGTCAGTC |
| 1461 | NFKB2-63 | CATTTAGCAGCAAGGTC |
| 1462 | NFKB2-64 | GCAGCATTTAGCAGC |
| 1463 | NFKB2-65 | CTGAGCAGCATTTAG |
| 1464 | NFKB2-66 | CCCATGAGAATCCT |
| 1465 | NFKB2-67 | CCTTCCCATGAGAATCC |
| 1466 | NFKB2-68 | TCCTCCCCTTCCCA |
| 1467 | NFKB2-69 | GCCTCCAGTAGACC |
| 1468 | NFKB2-70 | GTCAGACAGGGCCT |
| 1469 | NFKB2-71 | CCATGTCAGACAGG |
| 1470 | NFKB2-72 | GGCCCATGTCAGAC |
| 1471 | TANK-1 | GCTATTCCTGAAAATCAC |
| 1472 | TANK-2 | CCTCTTGTCTTCTTACC |
| 1473 | TANK-3 | GGAGAAGAAACCTCTTG |
| 1474 | TANK-4 | CCTTGCTGAAGTTTCTT |
| 1475 | TANK-5 | CCAAGACTCCTTGC |
| 1476 | TANK-6 | CCCTTTCATGGAGC |
| 1477 | TANK-7 | CCTCTTGGTGTGAC |

FIG. 5-6

| | | |
|---|---|---|
| 1478 | TANK-8 | GACTAAGGATGCCG |
| 1479 | TANK-9 | GTGGCAGGACTAAGG |
| 1480 | TANK-10 | AGACGTGGCAGGAC |
| 1481 | I-kappa-Bepsilon-1 | CTTCCAGCAGGCAG |
| 1482 | I-kappa-Bepsilon-2 | GTTCCTCTGCCTGG |
| 1483 | I-kappa-Bepsilon-3 | GATGTTCCTCTGCTG |
| 1484 | I-kappa-Bepsilon-4 | GAGATGTTCCTCTGCC |
| 1485 | I-kappa-Bepsilon-5 | GTGAGATGTTCCTCTG |
| 1486 | I-kappa-Bepsilon-6 | CAGAGAGTGAGATGTTCC |
| 1487 | I-kappa-Bepsilon-7 | CCAGAGAGTGAGATGTTC |
| 1488 | I-kappa-Bepsilon-8 | GGTCCAGAGAGTGAG |
| 1489 | I-kappa-Bepsilon-9 | GAGGTCCAGAGAGTG |
| 1490 | I-kappa-Bepsilon-10 | GGTCCTGTAGTGCC |
| 1491 | TRAF-6-1 | GATTTTATGATGCAGGC |
| 1492 | TRAF-6-2 | GACCTGCATCCCTTATTG |
| 1493 | TRAF-6-3 | TAGTTGATTTTCCAGCAG |
| 1494 | TRAF-6-4 | GAATCTCACGTTTTGC |
| 1495 | TRAF-6-5 | CAGAGAAAGAATCTCACG |
| 1496 | TRAF-6-6 | TTTCACCATCAGAGAAAAG |
| 1497 | TRAF-6-7 | CATTTGGACATTTCACC |
| 1498 | TRAF-6-8 | CCTTCATTTGGACATTTC |
| 1499 | TRAF-6-9 | CAATGTGCTTGATGATCC |
| 1500 | Rank-1 | CGCATCGGATTTCTC |
| 1501 | Rank-2 | CAAACCGCATCGGATTTC |
| 1502 | Rank-3 | GAACTGCAAACCGC |
| 1503 | Rank-4 | GCAGAGAAGAACTGC |
| 1504 | Rank-5 | GCAAGTAAACATGGG |
| 1505 | Rank-6 | GGTCCACGTTTTGG |
| 1506 | Rank-7 | GCAAGGGTCCACGTTT |
| 1507 | Rank-8 | TGCCTTCTTCTTCAGGG |
| 1508 | Rank-9 | TCCTGCTGGCTTCTTC |
| 1509 | Rank-10 | GTCCTGCTGGCTTC |
| 1510 | IL-5-1 | GGTAGTCTAGGAATTGG |
| 1511 | IL-5-2 | CTTGCAGGTAGTCTAGG |
| 1512 | IL-5-3 | GAAACTCTTGCAGGTAG |
| 1513 | IL-5-4 | CACCAAGAAACTCTTGC |
| 1514 | IL-5-5 | CATTACACCAAGAAACTC |
| 1515 | IL-5-6 | CTCGGTGTTCATTACACC |
| 1516 | IL-5-7 | CTTTCTATTATCCACTCG |
| 1517 | IL-5-8 | CCAGTTTAGTCTCAACTT |
| 1518 | IL-5-9 | AACCAGTTTAGTCTCAAC |

FIG. 5-7

| | | |
|---|---|---|
| 1519 | IL-5-10 | ACAAACCAGTTTAGTCTC |
| 1520 | IL-13-1 | CTCGCGAAAAAGTTTCTT |
| 1521 | IL-13-2 | CCCTCGCGAAAAAGTTTC |
| 1522 | IL-13-3 | GTCCCTCGCGAAAAAG |
| 1523 | IL-13-4 | CAGTTGAACCGTCCC |
| 1524 | IL-13-5 | GCTTTCGAAGTTTCAGTT |
| 1525 | IL-13-6 | GATGCTTTCGAAGTTTC |
| 1526 | IL-13-7 | CTGTCTCTGCAAATAATG |
| 1527 | IL-15-1 | CACTTATTACATTCACCC |
| 1528 | IL-15-2 | TTTTCCTCCAGTTCCTC |
| 1529 | IL-15-3 | GGACAATATGTACAAAACTC |
| 1530 | IL-15-5 | GTTGATGAACATTTGGAC |
| 1531 | IL-15-5 | GTGTTGATGAACATTTGG |
| 1532 | I-kappaB(newmember)-1 | CAAAATTTGGCCAGGG |
| 1533 | I-kappaB(newmember)-2 | GCCCAAAATTTGGCC |
| 1534 | I-kappaB(newmember)-3 | CCCAGCCCAAAATTTGG |
| 1535 | I-kappaB(newmember)-4 | GTCCCCAGCCCAAAATT |
| 1536 | I-kappaB(newmember)-5 | AAATCGCCAGAGGCTG |
| 1537 | I-kappaB(newmember)-6 | ACCAAATCGCCAGAGG |
| 1538 | I-kappaB(newmember)-7 | CATCACCAAATCGCCAG |
| 1539 | Prostaglan.Rec.EP3-1 | TAGGAGTGGTTGAGGC |
| 1540 | Prostaglan.Rec.EP3-2 | GTGTAGGAGTGGTTGAG |
| 1541 | Prostaglan.Rec.EP3-3 | CTGTGTAGGAGTGG |
| 1542 | Prostaglan.Rec.EP3-4 | CCCACATGCCTGTG |
| 1543 | Prostaglan.Rec.EP3-5 | CGATGAACAACGAG |
| 1544 | Prostaglan.Rec.EP3-6 | CTGGCGATGAACAACG |
| 1545 | Prostaglan.Rec.EP3-7 | CGCTGGCGATGAAC |
| 1546 | Prostaglan.Rec.EP3-8 | GAGCTAGTCCCGTTG |
| 1547 | Prostaglan.Rec.EP3-9 | GCGAAGAGCTAGTCC |
| 1548 | Prostaglan.Rec.EP3-10 | CCAGTTATGCGAAGAGC |
| 1549 | Prostaglan.Rec.EP3-11 | CCCCAGTTATGCGAAG |
| 1550 | PresenilinI-1 | CACATGCTTGGCGC |
| 1551 | PresenilinI-2 | CATCACATGCTTGGCG |
| 1552 | PresenilinI-3 | GACAAAGAGCATGATCAC |
| 1553 | PresenilinI-4 | GAGTCACAGGGACAAAG |
| 1554 | PresenilinI-5 | GAGAGTCACAGGGAC |
| 1555 | PresenilinI-6 | GCAGAGAGTCACAGG |
| 1556 | PresenilinI-7 | CCATGCAGAGAGTC |
| 1557 | PresenilinI-8 | CCACCATGCAGAGAG |
| 1558 | PresenilinI-9 | TAGCCACGACCACC |
| 1559 | PresenilinI-10 | GATTAGCTGCCCATCCTT |

FIG. 5-8

| | | |
|---|---|---|
| 1560 | PresenilinI-11 | GGTATAGATTAGCTGCC |
| 1561 | PresenilinI-12 | GTATCTTCTGTGAATGGG |
| 1562 | PresenilinI-13 | CTGGCCCACAGTCT |
| 1563 | PresenilinI-14 | CTCTGGCCCACAGT |
| 1564 | PresenilinI-15 | TGCAGGGCTCTCTG |
| 1565 | PresenilinI-16 | AGTGCAGGGCTCTC |
| 1566 | PresenilinI-17 | CACTGATCATGATGGC |
| 1567 | PresenilinI-18 | GACACTGATCATGATGGC |
| 1568 | PresenilinI-19 | ACAATGACACTGATCATG |
| 1569 | PresenilinI-20 | GAACCACCAGGAGGAT |
| 1570 | PresenilinI-21 | GACACAAAACAGCCACT |
| 1571 | PresenilinI-22 | GTGGACCTTTCGGAC |
| 1572 | PresenilinI-23 | CAACCAGCATACGAAGT |
| 1573 | PresenilinI-24 | TCCCTCTGGGCTTC |
| 1574 | PresenilinI-25 | ACTGTCCCTCTGGG |
| 1575 | PresenilinI-26 | GACTGTCCCTCTGG |
| 1576 | PresenilinI-27 | CCTAGATGACTGTCCC |
| 1577 | PresenilinI-28 | CAGCGAGGATACTGC |
| 1578 | PresenilinI-29 | CTTCACCAGCGAGGAT |
| 1579 | PresenilinI-30 | TTTCCTCTGGGTCTTCAC |
| 1580 | PresenilinI-31 | CTTTCCTCTGGGTCTTC |
| 1581 | PresenilinI-32 | CTCCCAATCCAAGTTTT |
| 1582 | TRADD-1 | TTCATCCCCGGAGCC |
| 1583 | TRADD-2 | TTCTTCATCCCGGAGC |
| 1584 | TRADD-3 | GCTCAGCCAGTTCTTC |
| 1585 | TRADD-4 | GACAGAGAGGGCAC |
| 1586 | TRADD-5 | CTTCACCTCCGACAG |
| 1587 | TRADD-6 | GAAAAGTCTGGGCAGG |
| 1588 | TRADD-7 | GACCCTGGAACAGAAAAG |
| 1589 | TRADD-8 | CTGACCCTGGAACAG |
| 1590 | TRADD-9 | ACTACAGGCTGACCCT |
| 1591 | TRADD-10 | ATTCACTACAGGCTGACC |
| 1592 | TRADD-11 | CGATTCACTACAGG |
| 1593 | TRADD-12 | GGCCGATTCACTAC |
| 1594 | TRADD-13 | CGAACGTCTGTTGGTC |
| 1595 | TRADD-14 | CGCGAACGTCTGTTG |
| 1596 | PKA-1 | CTTCTGTTTGTCGAGGAT |
| 1597 | PKA-2 | TTCACCACCTTCTGTTTG |
| 1598 | PKA-3 | AGGATGCGCTTTTCATTC |
| 1599 | PKA-4 | AGCTTGCAGGATGCG |
| 1600 | PKA-5 | GTTGACAGCTTGCAGGAT |

FIG. 5-9

| | | |
|---|---|---|
| 1601 | PKA-6 | GGAACGGAAAGTTGACAG |
| 1602 | PKA-7 | AACTCGAGTTTGACGAGG |
| 1603 | PKA-8 | TGTCCTTGAAGGAGAAC |
| 1604 | PKA-9 | CGTACTCCATGACCATGT |
| 1605 | PKA-10 | GCACGTACTCCATGAC |
| 1606 | PKA-11 | GATTCTCCGGCTTCAG |
| 1607 | PKA-12 | TCAATGAGCAGATTCTCC |
| 1608 | PKA-13 | GGTCAATGAGCAGATTC |
| 1609 | PKA-14 | CCCTGCTGGTCAATG |
| 1610 | PKA-15 | TAGCCCTGCTGGTC |
| 1611 | PKA-16 | CGCTTGGCGAAACC |
| 1612 | PKA-17 | CCTTCACGCGCTTG |
| 1613 | PKA-18 | AAGGTCCAAGTGCG |
| 1614 | PKA-19 | TGCCGCACAAGGTC |
| 1615 | IL-12alpha-1 | GGTGAGGACCACCATTT |
| 1616 | IL-12alpha-2 | GGGTGTCACAGGTG |
| 1617 | IL-12alpha-3 | ATACCATCTTCTTCAGGG |
| 1618 | IL-12alpha-4 | GGTGATACCATCTTCTTC |
| 1619 | IL-12alpha-5 | CCAGGTGATACCATCTTC |
| 1620 | IL-12alpha-6 | CCTCACTGCTCTGGT |
| 1621 | IL-12alpha-7 | TAAGACCTCACTGC |
| 1622 | IL-12alpha-8 | CAGAGCCTAAGACCTC |
| 1623 | IL-12alpha-9 | CCAGAGCCTAAGACC |
| 1624 | IL-12alpha-10 | TCTTCCTTTTTGTGAAGC |
| 1625 | IL-12alpha-11 | GACCAAATTCCATCTTCC |
| 1626 | IL-12alpha-12 | ATCAGTGGACCAAATTCC |
| 1627 | IL-12alpha-13 | GGTTCTTCTGGTCCTTT |
| 1628 | IL-12alpha-14 | TTTTTGGGTTCTTCTGG |
| 1629 | IL-12alpha-15 | GGTCTTATTTTGGGTTC |
| 1630 | IL-12alpha-16 | AATGGGCAGACTCTCCT |
| 1631 | IL-12alpha-17 | TCCACCATGACCTCAATG |
| 1632 | IL-12alpha-18 | AACGGCATCCACCATG |
| 1633 | IL-12alpha-19 | GTGAACGGCATCCAC |
| 1634 | IL-12alpha-20 | ACTTGAGCTTGTGAACGG |
| 1635 | IL-12alpha-21 | TTCATACTTGAGCTTGTG |
| 1636 | IL-12alpha-22 | CTGGTGTAGTTTTCATAC |
| 1637 | IL-12alpha-23 | AGCTGCTGGTGTAGTTTT |
| 1638 | IL-12beta-1 | AGGAGGACCAGGGT |
| 1639 | IL-12beta-2 | AGGTGGTCCAGGAG |
| 1640 | IL-12beta-3 | TTTCTGGCCAAACTGAGG |
| 1641 | IL-12beta-4 | GGAGGTTTCTGGCC |

FIG. 5-10

| | | |
|---|---|---|
| 1642 | IL-12beta-5 | TCTGGAGTGGCCAC |
| 1643 | IL-12beta-6 | CTTCTGGAGCATGTTGCT |
| 1644 | IL-12beta-7 | GCCTTCTGGAGCATG |
| 1645 | IL-12beta-8 | GTTTGTCTGGCCTTCTG |
| 1646 | IL-12beta-9 | GAGTTTGTCTGGCCTTCT |
| 1647 | IL-12beta-10 | CTAGAGTTTGTCTGGCCT |
| 1648 | IL-12beta-11 | GCAAGGGTAAAATTCTAG |
| 1649 | IL-12beta-12 | AGTGCAAGGGTAAAATTC |
| 1650 | IL-12beta-13 | AAACAGGCCTCCACT |
| 1651 | IL-12beta-14 | CTTGGTTAATTCCAATGG |
| 1652 | IL-12beta-15 | AGGCAACTCCCATTAGTT |
| 1653 | IL-12beta-16 | TACTACTAAGGCACAGGG |
| 1654 | IL-12beta-17 | AATACTACTAAGGCACAG |
| 1655 | IL-12beta-18 | GTACATCTTCAAGTCTTC |
| 1656 | Pg-R | GGAGTGGACATGAT |
| 1657 | thr | AAGAAGATGAAGCCTTTG |
| 1658 | ref-fosjun | CCGTCTTACTCTTCTTGG |
| 1659 | PIV | CCGATACAATTCCAAGG |
| 1660 | PIV | CCTTTTCCTTCTGAG |
| 1661 | PIV | CTGTTGCAAGTACG |
| 1662 | bak | CAGAAGCAGAGGGC |
| 1663 | bak | CCTCAGAAGCAGAGG |
| 1664 | bak | CTCCTCAGAAGCAG |
| 1665 | bak | ACAGGCTGGTGGCA |
| 1666 | bak | CCACTCTCAAACAGGC |
| 1667 | bak | ACGGTAGCCGAAGC |
| 1668 | bak | GACGGTAGCCGAAGC |
| 1669 | bak | GGCCAGACGGTAGC |
| 1670 | bak | GTGTAGGGCCAGACGGTA |
| 1671 | bak | CCGAAGCCATTTTTCAGG |
| 1672 | bak | CCCCGAAGCCATTTTTC |
| 1673 | bak | GGTTGATGTCGTCC |
| 1674 | bak | GCTTGAGACACTCGC |
| 1675 | bak | CCGGACCCGTCCAT |
| 1676 | bclx | GCTTGCTTTACTGC |
| 1677 | bclx | GGTTGCTCTGAGAC |
| 1678 | bclx | GCCACAGTCATGCC |
| 1679 | bmp | CGGGCATGCTGGCG |
| 1680 | bmp | GTGAAGTTCAGGATGATC |
| 1681 | bmp | CCAGTGCCTCATGG |
| 1682 | ICE | CAGTGTTCTCCATGG |

FIG. 5-11

| | | |
|---|---|---|
| 1683 | ICE | CTGTACCAGACCGAG |
| 1684 | ICE | GCATACTGTTTCAGC |
| 1685 | ich | GCCATCAGCTCCTTG |
| 1686 | ich | CCACACCATAGATGG |
| 1687 | ich | GCTGGAGCAGTTTCC |
| 1688 | bcl1 | CTCGCTTCTGCTGC |
| 1689 | bcl2 | ACCGTGGCAAAGCG |
| 1690 | mucrep | AGGTGACACCGTGG |
| 1691 | AHR | GACTTGATTCCTTCAG |
| 1692 | AHR | GGATTTGACTTGATTCC |
| 1693 | AHR | GCTGCTGTTCATGG |
| 1694 | CD2 | CCGTTTCTTTCAGTAGG |
| 1695 | MEK2 | CTTGAAGTAGGAGC |
| 1696 | tnf | CGCTCCTACATGGC |
| 1697 | tnf | GATGAGGTACAGGCC |
| 1698 | tnf | GTAGATGAGGTACAG |
| 1699 | tnf | GAGTAGATGAGGTAC |
| 1700 | tnf | CCTGGGAGTAGATG |
| 1701 | tnf | GGACCTGGGAGTAG |
| 1702 | tnf | ACATGGGTGGAGGG |
| 1703 | tnf | GTGCTCATGGTGTC |
| 1704 | tnf | CTTTCAGTGCTCATG |
| 1705 | tnf | TGCTTTCAGTGCTCA |
| 1706 | tnf | GATGATCTGACTGCC |
| 1707 | tnf | GTTCGAGAAGATGATC |
| 1708 | tnf | GGGTTCGAGAAGATG |
| 1709 | tnf | GGTTTGCTACAACATG |
| 1710 | tnf | CAGCTTGAGGGTTTG |
| 1711 | tnf | TGCCCCTCAGCTTG |
| 1712 | TNFR | GACACACACTATCTC |
| 1713 | IL-18 | GCAGCCATCTTTATTC |
| 1714 | IL-18 | GTTCAGCAGCCATC |
| 1715 | IL-18 | TGGTTCAGCAGCCA |
| 1716 | IL-18 | CTACTGGTTCAGCAGC |
| 1717 | IL-18 | TCTACTGGTTCAGC |
| 1718 | IL-18 | GCCACAAAGTTGATGC |
| 1719 | IL-18 | CATTGCCACAAAGTTG |
| 1720 | IL-18 | GAGAACTTGGTCATTC |
| 1721 | IL-18 | GGTCAATGAAGAGAAC |
| 1722 | IL-18 | CGATTTCCTTGGTC |
| 1723 | IL-18 | CCGATTTCCTTGGTC |

FIG. 5-12

| | | |
|---|---|---|
| 1724 | IL-18 | CAAATAGAGGCCGATTTC |
| 1725 | IL-18 | CAAATAGAGGCCGA |
| 1726 | IL-18 | CCTCTAGGCTGGCT |
| 1727 | IL-18 | CATACCTCTAGGCTG |
| 1728 | IL-18 | AGCCATACCTCTAG |
| 1729 | IL-18 | CAGCCATACCTCTAG |
| 1730 | IL-18 | CACAGAGATAGTTACAG |
| 1731 | IL-18 | GTCTTCGTTTTGAACAG |
| 1732 | IL-18 | CTAGTCTTCGTTTTGAAC |
| 1733 | IL-18 | TAGCTAGTCTTCGTTTTG |
| 1734 | IL-18 | GAGCCACTGCGCC |
| 1735 | IL-18 | CGTGAGCCACTGCG |
| 1736 | IL-12-Rec | CGTAACGATCACTGG |
| 1737 | IL-12-Rec | GCACTCGTAACGATC |
| 1738 | IL-12-Rec | GGAGCACTCGTAAC |
| 1739 | IL-12-Rec | CATCATCCTGAGGT |
| 1740 | IL-12-Rec | CAGTATCATCATCCTG |
| 1741 | IL-12-Rec | CTCAGTATCATCATCC |
| 1742 | IL-12-Rec beta2 | CTAAAAGTATGTGCCATC |
| 1743 | IL-12-Rec beta2 | CACATCGCCTCTCT |
| 1744 | IL-12-Rec beta2 | GCTTCACAGTCACATCGC |
| 1745 | IL-12-Rec beta2 | GGAAGGCTTCACAGTC |
| 1746 | IL-12-Rec beta2 | CCTGTGACTTGAGAATTG |
| 1747 | IL-12-Rec beta2 | GGAAGACCTGTGAC |
| 1748 | IL-12-Rec beta2 | CTCTGCTCCACATATTTG |
| 1749 | IL-12-Rec beta2 | CAACGAAGATCTCTG |
| 1750 | IL-12-Rec beta2 | CAACACCAACGAAG |
| 1751 | PKC-beta | GGTCTTCTGTTTGC |
| 1752 | CB-1-Rec | CGATGAAGTGGTAGGAAG |
| 1753 | TGF-alpha | GGTTGCATGGAAGC |
| 1754 | Fascin | GGTCACAAACTTGCC |
| 1755 | p300 | CTGATTTGGTCCACTAG |
| 1756 | CBP | CATGTTAGCACTGTTC |
| 1757 | rac-alpha | GGTCTTGATGTACTCC |
| 1758 | EBV | CCACCTAAAGAGAGATC |
| 1759 | HSPQ | CTTGTACTGCACCATC |
| 1760 | CC-CKR1 | GCCAGTTAAGAAGATG |
| 1761 | CC-CKR4 | GAGATCATGATCCATGG |
| 1762 | c-CRK | GTAGTGTCCCAATAGTG |
| 1763 | c-CRK | CTTCCTCATCATTCCC |
| 1764 | CRKL | CACAAGCTTTTCGAC |

ANTISENSE OLIGONUCLEOTIDE PREPARATION METHOD

This application is a 371 of PCT EP 98/00497, Jan. 30, 1998.

The present invention is related to a method for the preparation of antisense oligonucleotides and to an oligonucleotide or functional or structural analogs or effective derivatives thereof, forming hydrogen bonds with deoxyribonucleic acids (DNA) and/or ribonucleic acids (RNA) or derivatives thereof including, but not limited to the formation of hydrogen bonds with the bases adenine (A), cytosine (C), guanine (G), uracil (U) or thymidine (T) contained in such molecules or forming hydrogen bonds with residues of a particular protein, such a molecule being capable of altering the expression structure or function, of a gene, an RNA molecule or a protein or altering the level of activity of a gene, an RNA molecule or a protein. Furthermore, the present invention is related to such nucleic acid or functional or structural analogs or effective derivatives thereof, coupled or mixed with folic acid, hormones, steroid hormones such as oestrogen, progesterone, corticosteroids, mineralocorticoids, androgens, peptides, proteoglycans, phospholipids, glycolipids and derivatives therefrom.

Furthermore, the invention is related to the use of said nucleic acids or functional or structural analogs or effective derivatives thereof, for analyzing the functional properties of a particular gene, RNA, or protein by altering its activity, structure, function or altering its expression levels.

Furthermore, the invention is related to antisense nucleic acids, capable of modulating the expression or functional activity of proteins which regulate cell growth leading to augmentation, inhibition or modulation of cell growth or cell proliferation and/or the expansion of primary cells or stem cells, e.g. in culture or in the living organism.

Furthermore, the invention is related to a pharmaceutical composition comprising said nucleic acids or functional or structural analogs or effective derivatives thereof, hybridizing with an area of the messenger RNA (mRNA) or the DNA of a target gene or binding to a particular protein as well as the use of said nucleic acids, structural analogs and derivatives thereof for the manufacturing of a pharmaceutical composition for the treatment of diseases where the alteration of the structure function, activity or expression of a particular target gene, a particular target RNA or a particular target proteins activity leads to a therapeutic benefit related to the effect of the nucleic acid or derivative thereof.

Modulation of the expression of genes, RNA molecules or proteins or of their activity levels with nucleic acids or functional or structural analogs or effective derivatives thereof is a powerful means to study the function of the respective molecules. For example modulation, e. g. knockdown or increase of the expression of a particular protein can lead to the identification of its physiological as well as its pathophysiological roles in cultured cells as well as in living organisms in vivo.

Furthermore, the aberrant expression or overexpression of genes, RNA molecules or proteins, the expression of foreign DNA, RNA or proteins e. g. derived from infectious organisms or the expression of mutated DNA, RNA and proteins is found in a variety of diseases. Downregulation of the expression or the activity of such DNA, RNA and/or proteins can lead to an inhibition of or to the reversal of pathological processes in which the expression of a particular DNA, RNA and/or protein plays a role. However, nucleic acids or derivatives thereof used for downregulation of DNA, RNA and/or protein expression are often ineffective and/or toxic to the cells or the organisms treated with such molecules.

An object of the present invention is to provide a method for designing and preparation of oligonucleotides or derivatives thereof which avoid the drawbacks of prior art, and give a reliable method for preparation of oligonucleotides having increased effectivity and/or reduced toxicity and/or reduced non-selective effects.

The object is attained by a method having the features of claim 1. Preferred embodiments of the method of the invention are those according to claims 2 to 7.

The method of the invention comprises the steps of selecting a target nucleic acid, if necessary elucidating its sequence generating the antisense oligonucleotide with the proviso that the oligonucleotide comprises at least 8 residues, the oligonucleotide comprises at maximum twelve elements, which are capable of forming three hydrogen bonds each to cytosine bases, the oligonucleotide does not contain four or more consecutive elements, capable of forming three hydrogen bonds each with four consecutive cytosine bases (CCCC) within the target molecule or alternatively four or more consecutive elements of GGGG, the oligonucleotide does also not contain 2 or more series of three consecutive elements, capable of forming three hydrogen bonds each with three consecutive cytosine bases (CCC) within the target molecule, or alternatively 2 or more series of three consecutive elements of GGG, and the ratio between residues forming two hydrogen bonds per residue (2H-bond-R) with the target molecule and those residues forming three hydrogen bonds per residue (3H-bond-R) with the target molecule, is ruled by the following specifications:

$$\frac{3H\text{-bond-}R}{3H\text{-bond-}R + 2H\text{-bond-}R} \geq 0.29$$

and synthesizing the oligonucleotide thus generated in a per se known manner.

The generated antisense oligonucleotide comprises at least 8 residues in order to have sufficient interaction with the target molecule and has preferably up to 30, more preferably up to 24 or most preferred upt to 18 residues. Shorther chain length are preferred over longer ones to increase specifity and/or reduce non-specific effects.

The oligonucleotide comprises at maximum 12 elements which are capable of forming 3 hydrogen bonds each to cytosine bases. In case of generating an oligonucleotide an element is represented by a residue, thus a nucleotide of the oligonucleotide. In cases of generating a derivative an element is considered as a part of the molecule capable of forming hydrogen bonds. It is preferred that the oligonucleotide comprises at maximum 10 and more preferred at maximum 8 elements which are capable of forming 3 hydrogen bonds each to cytosine bases.

The generated antisense oligonucleotide preferably does not contain 4 or more consecutive guanine bases and does also not contain 2 or more series of 3 consecutive guanine bases.

Preferably, the ratio between residues forming 2 hydrogen bonds per residue (2H-bond-R) with their target molecule and those residues forming 3 hydrogen bonds per residue (3H-bond-R):

$$\frac{3H\text{-bond-}R}{3H\text{-bond-}R + 2H\text{-bond-}R}$$

is in the range of greater than 0.33 and smaller than 0.86, more preferably smaller than 0.79 and still more preferred smaller than 0.72.

In one embodiment the oligonucleotides generated by the method of the invention are modified for higher nuclease resistance than naturally occurring nucleotides. Methods for synthezing oligonucleotides and derivatives thereof are known in the art, see for exammple "Oligonucleotides and Analogues", F. Eckstein (Ed.), 1991, IRL Press Oxford or "Protocols for Oligonucleotides and Analogs, Synthesis and Properties", Sudhir Agrawal (Ed.), 1993, Humana Press, Totowa, N.J.

Oligonucleotides of the invention may also contain RNA and DNA residues within their chains.

The modifications can be made to the bases, the sugars or the linkages of the oligonucleotides. Preferably, the modifications are phosphorothioate (S-ODN) internucleotide linkages, and/or methylphosphonate internucleotide linkages, N'3->P5' phosphoramidate linkages, peptide linkages or 2'-methoxyethoxy modifications of the sugar moiety or modifications of the bases. In a preferred embodiment the oligonucleotide has at least two different types of modifications and more preferably at least two different types of internucleotide linkages. In another preferred embodiment the oligonucleotides are linked to or mixed with folic acid, hormones such as steroid hormones or corticosteroids, peptides, proteoglycans, glycolipids, phospholipids or derivatives thereof.

Surprisingly the molecules, obtainable according to the method of the invention could strongly reduce or avoid toxicity and/or non-specific effects of such molecules and/or had significantly higher activity than sequences selected otherwise. Preferably, the molecules according to the invention have the following features: They do not contain four or more consecutive guanosine ($N_aGGGGN_b$) or inosine ($N_aIIIIN_b$) residues and the oligonucleotide does not contain two or more series of three or more consecutive guanosine residues ($N_aGGGN_cGGGN_b$) and does not contain two ore more series of three or more consecutive inosine residues ($N_aIIIN_cIIIN_b$), wherein $N_a$, $N_b$, $N_c$ represent indepently oligonucleotides of any sequence having 0 to 20 residues.

In a preferred embodiment the molecule contains a minimum of 10 residues capable of forming either two or three hydrogen bonds per residue. Furthermore, the molecule contains a maximum of 24 consecutive residues linked by phosphorothioate linkages capable of forming either two or three hydrogen bonds per residue. In molecules according to the invention which contain more than 18 residues the additional linkages preferably consist of methylphosphonate linkages or phosphodiester linkages.

The chemical structures of antisense oligodeoxyribonucleotides are given in FIG. 1.

Figure 2:
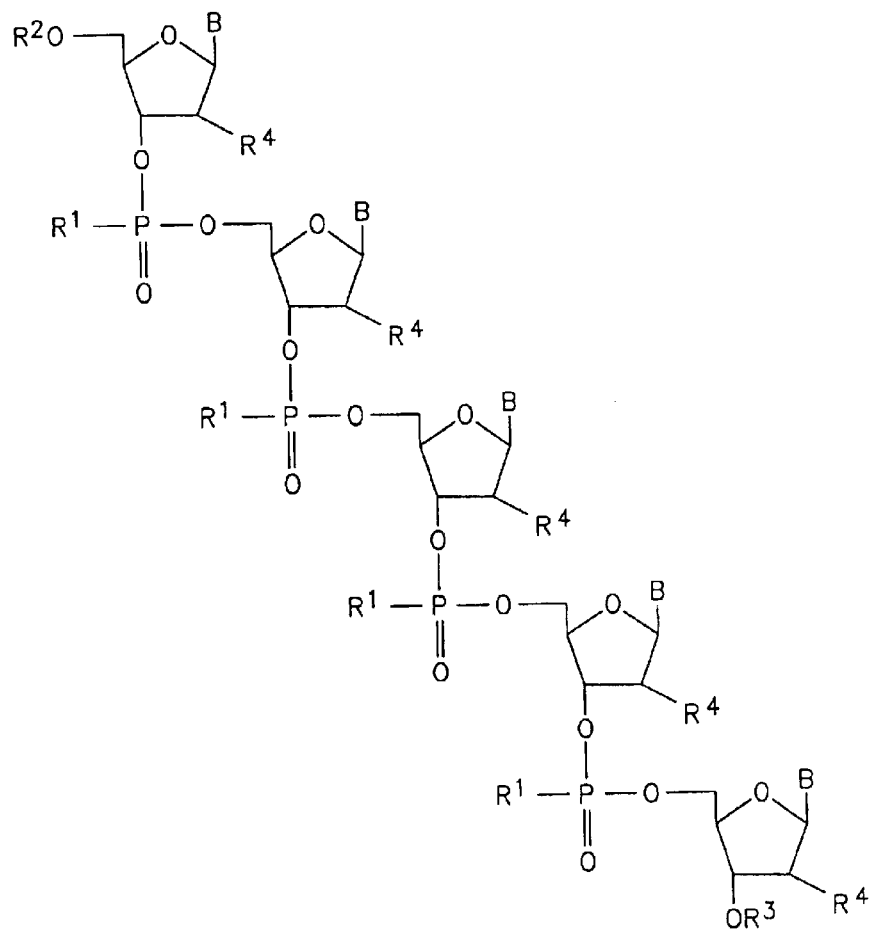

The chemical structures of antisense oligoribonucleotides are given in FIG. 2. The oligonucleotide is to be understood as a detail out of a longer nucleotide chain.

Of course, the oligonucleotides may be composed of elements of either figures.

In FIGS. 1 and 2, lit. B means an organic base such as adenine (A), guanine (G), cytosine (C), inosine (I), uracil (U) and thymine (T) which are coupled to the deoxyribose. The linkages between the nucleotides are either phosphodiester bonds as in naturally occurring DNA or linkages spacing the nucleotides in such a way to allow hybridization with its target nucleic acid or binding to a protein in order to regulate its activity, such as e.g. phosphorothioate linkages, methylphosphonate linkages, phosphoramidate linkages or peptide linkages.

$R_2$ and $R_3$ represent further residues of the oligonucleotide or derivative.

$R_4$ represents OH or a modification such as a 2'-methoxy ethoxy derivative.

The modifications of the phosphodiester linkage, shown in FIGS. 1 and 2 can be selected from, but are not limited to.

1. Oligodeoxy-ribonucleotides or oligoribionucleotides substituted by
   1.1. R1=O
   1.2. R1=S
   1.3. R1=F
   1.4. R1=$CH_3$
   1.4. R1=OEt
2. oligodeoxy-ribonucleotides where R1 is varied at the internucleotide phosphates within one oligonucleotide

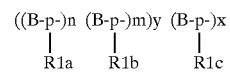

where lit. p stands for the phosphodiester or the phosphoramidate linkage, modified by coupling to R1a, R1b or R1c or for a peptide linkage, or for linkages spacing the nucleotides in such a way to allow hybridization with its target nucleic acid or binding to a protein in order to regulate its activity, structure, function or expression level.

where lit. B=any deoxy-ribonucleotide or ribonucleotide depending on gene sequence according to the invention.

n, m, x, y=integers 0–20

Preferred maximal length of the total number of bases is 30.

| | | | |
|---|---|---|---|
| 2.1 | $R_{1a}=S$ | $R_{1b}=CH_3$ | $R_{1c}=S$ |
| 2.2 | $R_{1a}=S$ | $R_{1b}=CH_3$ | $R_{1c}=O$ |
| 2.2 | $R_{1a}=S$ | $R_{1b}=O$ | $R_{1c}=S$ |
| 2.2 | $R_{1a}=S$ | $R_{1b}=O$ | $R_{1c}=CH_3$ |
| 2.3 | $R_{1a}=CH_3$ | $R_{1b}=S$ | $R_{1c}=CH_3$ |
| 2 4 | $R_{1a}=CH_3$ | $R_{1b}=S$ | $R_{1c}=O$ |
| 2.5 | $R_{1a}=CH_3$ | $R_{1b}=O$ | $R_{1c}=CH_3$ |
| 2.6 | $R_{1a}=CH_3$ | $R_{1b}=O$ | $R_{1c}=S$ |
| 2.7 | $R_{1a}=O$ | $R_{1b}=S$ | $R_{1c}=O$ |
| 2.8 | $R_{1a}=O$ | $R_{1b}=S$ | $R_{1c}=CH_3$ |
| 2.9 | $R_{1a}=O$ | $R_{1b}=CH_3$ | $R_{1c}=O$ |
| 2.10 | $R_{1a}=O$ | $R_{1b}=CH_3$ | $R_{1c}=S$ |

Preferably, the oligonucleotide comprises a minimum of 10 elements and a maximum of 24 elements capable of forming either 2 or 3 hydrogen bonds per element. The oligonucleotides of the invention can have modifications to the base, the sugar or the phosphate moiety. Preferred modifications are phosphorothioate (S-ODN) internucleotide linkages, and/or methylphosphonate internucleotide linkages, N'3->P5' phosphoramidate linkages, peptide linkages or 2'-methoxyethoxy modifications of the sugar or modifications of the bases. In a very preferred embodiment the antisense oligonucleotides comprise the sequences 41 to 73, 74 to 106, 154 to 172, 173 to 203, 298 to 380, 476 to 506, 519 to 556 and 597 to 641 of FIG. 3 and 1273–1764 of FIG. 5. A further aspect of the invention is the use of the oligonucleotides of the invention for the inhibition of the genes p53, rb, junD, junB, TGF-β1, TGF-β2 to influence cell proliferation, in particular of primary cell cultures such as liver cells, kidney cells, osteoclasts, osteoblasts and/or keratinocytes and/or cells of the blood lineage, such as bone marrow stem cells, and/or progenitor cells of red and white blood cells and/or organ stem cells.

The Sequences 41–73 and/or 74–106 and/or 154–203 and/or 519–556 and/or 597–641 and/or 1273–1277 and/or 1481–1490 and/or 1532–1549 and/or 1656 are useful for the treatment and/or prevention of immunosuppressive disorders including, but not limited to immunosuppression in neoplastic diseases—including gliomas and other brain tumors, sarcomas, carcinomas and lymphomas—and/or immunosuppression as side effect from drugs, including, but not limited to side effects from cytotoxic agents and/or immunosuppression in AIDS patients.

In a further embodiment of the invention these sequences are also useful for the treatment and/or prevention of hyoproliferation of normal cells, including, but not limited to immune cells, bone marrow stem cells, endothelial cells, organ stem cells and proliferating cells of the intestine.

The Sequences 41–73 and/or 74–106 and/or 298–380 and/or 476–506 and/or 519–556 and/or 1273–1480 and/or 1596–1614 and/or 1657–1658 and/or 1690 and/or 1696–1712 and/or 1751 and/or 1753–1754 and/or 1757 are useful for the treatment and/or prevention of hyperproliferative disorders, including but not limited to brain tumors, sarcomas, carcinomas and lymphomas, restenosis, hyperplasisa, pulmonary fibrosis, angiogenesis and psoriasis.

The Sequences 1278–1480 and/or 1491–1531 and/or 1582–1595 and/or 1615–1655 and/or 1691–1694 and/or 1697–1750 and/or 1759–1764 are useful for the treatment and/or prevention of diseases characterised by hyperfunction of the immune system and/or of inflammatory disorders and/or auto-immune disorders, including, but not limited to asthma (molecules according to the invention being applied by inhalation and/or by parenteral routes and/or orally), multiple sclerosis, inflammatory disorders of the intestine, including jejunitis, ileitis and/or colitis, as well as inflammatory disorders characterised by hyperproliferation and/or hyperfunction of cells of the eosinophilic lineage and/or glomerulonephritis and/or rejection of transplants.

The Sequences 476–506 and/or 1550–1581 and/or 1582–1595 and/or 1658–1689 and/or 1691–1694 and/or 1713–1752 are useful for the treatment and/or prevention of diseases associated with cell degeneration, including, but not limited to neurodegeneration, e.g. Alzheimer's diseases, Parkinson's, ischemic disorders, including myocardial ischemia and/or ischemia of the nervous system, including stroke.

A further aspect of the present invention is a medicament comprising an oligonucleotide according to the invention together with additives. The oligonucleotides of the invention can be used for the preparation of a medicament for the prevention or the treatment of neoplasm, hypoproliferation, hyperproliferation, degenerative diseases, neurodegenerative diseases, ischaemia, disorders of the immune system and/or infectious diseases and can be used for the analysis of gene function or drug target validation.

Molecules according to the invention can be used to study the function of target molecules and their encoded transcription and/or translation products, including RNA molecules and proteins. Downregulations of a protein or nucleic acid molecule using molecules according to the invention can be used to study the function of the molecule. It is also a feature of the invention that molecules according to the invention can be used to study whether modulation of the product has a desired effect, including therapeutic effects and to use this information to develop a different molecule, in order to modulate the function of the protein.

This includes, for example, drug target validation with a molecule according to the invention, in order to answer the question whether development of an agent capable of modulating the structure, function or expression of a potential target molecule, e. g. an agonist or antagonist of the target molecule has desired effect and may e. g. be of therapeutic or diagnostic use.

It is thus also a feature of the invention that molecules according to the invention can be used for drug target validation, including but not limited to studying whether modulation of a protein or nucleic acid molecule has a desired effect, including therapeutic effects and using this information to develop a compound, e. g. a therapeutic compound capable of modulating the structure, function or expression of the molecule the function of which was previously studied with molecules according to the invention.

EXAMPLE 1

Treatment of Peripheral Blood Mononuclear Cells with TGF-β1 Antisense Phosphorothioate Oligodeoxynucleotides:

Human peripheral blood mononuclear cells (PBMCs) produce transforming growth factor β1 (TGF-β1). The TGF-β1 produced by these cells negatively regulates immune cell proliferation in an autologous manner. This autologous negative regulation of immune cell proliferation could be reversed by antisense TGF-β1 molecules according to the invention, leading to stimulation of immune cell proliferation. In contrast to the molecules according to the invention, antisense molecules chosen conventionally, including that published by Hatzfeld et al. (1991) did not stimulate immune cell proliferation. Even more surprising, several sequences, chosen conventionally, even reduced immune cell proliferation.

Peripheral blood mononuclear cells (PBMCs) were isolated from venous blood of healthy donors by mixing with an equal volume of RPMI 1640 medium (Gibco) supplemented with 10% fetal calf serum and 1 mM L-glutamine, followed by layering onto Ficoll-Hypaque (Pharmacia) gradients and centrifugation at 400 g for 30 min. PBMCs were removed from the plasma-Ficoll interface and washed in the above medium. Cells (2×104 in 100 µl of medium) were plated into 96 well flat-bottom microtiter plates (Nunc) in serum supplemented complete medium. Cells were activated with 3 µg/ml phytohemagglutinin and incubated with either no oligodeoxynucleotide (untreated control cells) or with 8 µM of different antisense phosphorothioate oligodeoxynucleotides, complementary to different regions of the human TGF-β1 mRNA for 4 days. Cells were then stained with trypan blue to determine cell viability and counted in a Neubauer counting chamber.

Oligonucleotide sequences were either 33 sequences according to the invention, named sequences TGF-β1-1–TGF-1-33 (SEQ ID NOS: 41–73) or the TGF-β1 antisense sequence from Hatzfeld et al. (1991), J. Exp. Med., 174, pp. 925–929 or 39 other conventionally chosen antisense sequences complementary to human TGF-β1 nRNA, named N1–N39 (see FIG. 3) (SEQ ID NOS: 2–40).

Surprisingly the molecules according to the invention were much more effective than antisense TGF-β1 molecules that were chosen conventionally.

Sequences TGF-β1-1–TGF-β1-33 (SEQ ID NOS: 41–73) (see FIG. 3) enhanced lymphocyte proliferation to between 135 and 213% of untreated controls. In contrast, treatment with the antisense sequence from document Hatzfeld et al. reduced proliferation to 62.8%.

Cells treated with the conventionally chosen TGF-β1 antisense sequences N1–N39 (SEQ ID NOS: 2–40) surprisingly not only failed to increase lymphocyte proliferation, but several of these sequences even revealed a marked inhibition of cell proliferation to between 51.4% and 77% of controls (sequences N1–N14 (SEQ ID NOS: 2–15), N20 (SEQ ID NO: 21), N26 (SEQ ID NO: 27) and N30–N39 (SEQ ID NOS: 31–40). The antisense TGF-β1 sequences N15–N19, (SEQ ID NOS: 16–20) N21–N25 (SEQ ID NOS: 22–26), N28 (SEQ ID NO: 29) and N29 (SEQ ID NO: 30) showed neither significant enhancement nor significant inhibition of cell proliferation with values between 94% and 103%. Sequence N27 (SEQ ID NO: 28) showed slight toxicity with a reduction in cell proliferation to 88%.

Inhibition of cell proliferation by some of the TGF-β1 sequences suggests that they may not be merely ineffective, but also toxic. Analysis of the 26 sequences N1–N14 (SEQ ID NOS: 2–15), N20 (SEQ ID NO: 21), N26 (SEQ ID NO: 27) and N30–N39 (SEQ ID NOS: 31–40) revealed that 23 of them contained either 2 or more sequence motifs with three consecutive Gs (hereafter called GGG motif) or at least one motif with 4, 5, or 6 Gs (motifs GGGG, GGGGG, or GGGGGG). Analysis of the sequence from Hatzfeld et al., which also inhibited PBMC proliferation, surprisingly showed that it too contains a GGGGG plus a GGG motif. The 3 toxic sequences that contained neither 2 GGG motifs nor a motif of 4 or more consecutive Gs, i.e. sequences N8 (SEQ ID NO: 9), N26 (SEQ ID NO: 27), and N35 (SEQ ID NO: 36) were found have a base content with 11–13 G-bases per sequence.

In contrast to the sequences from Hatzfeld et al., N1–N14 (SEQ ID NOS: 2–15), N20 (SEQ ID NO: 21), N26 (SEQ ID NO: 27) and N30–N39 (SEQ ID NOS: 31–40) the sequences TGF-β1-1–TGF-β1-33 showed a G-content of maximally 6 G-bases, no combination of two GGG motifs within a single sequence and no GGGG, GGGGG or GGGGGG motif. Since the TGF-β1 mRNA contains more than 85 target regions for a GGG antisense motif and more than 34 target regions for a GGGG antisense motif, this finding in the sequences according to the invention was highly unlikely on a statistical basis.

The non-effective sequences N15–N19 (SEQ ID NOS: 16–20), N21–N25 (SEQ ID NOS: 22–26), N28 (SEQ ID NO: 29) and N29 (SEQ ID NO: 30) were found to contain a different base content from both the toxic and the effective sequences: They content of the bases A and T taken together (A/T-content) ranged from 14.3% to 28.5%. These sequences neither enhanced nor did they inhibit PBMC proliferation. Thus, they appeared to be neither effective nor toxic. In contrast to these non-effective sequences with an A/T content of 14.3%–28.5%, the effective sequences TGF-β1-1–TGF-β1-33 (SEQ ID NOS: 41–73) were found to have an A/T content of between 33%–71.4%.

A further difference between the sequences of the invention and two thirds of the other sequences was found with respect to non-specific protein binding: Sequences from document Hatzfeld et al. and N1–N14 (SEQ ID NOS: 2–15), N20 (SEQ ID NO: 21), N26 (SEQ ID NO: 27) and N30–N39 (SEQ ID NOS: 31–40) were found to show markedly enhanced non-specific protein binding compared to the sequences of the invention.

Sequences from Hatzfeld et al. (H) and N1–N39 (SEQ ID NOS: 2–40) are shown in FIG. 3 as well as TGF-β1 antisense sequences according to the invention.

The finding that, while the sequences TGF-β1-1–TGF-β1-33 (SEQ ID NOS: 41–73) stimulated proliferation of PBMC immune cells, the sequence from Hatzfeld et al. and sequences N1–N39 (SEQ ID NOS: 2–40) where either non-effective with little alteration in PBMC proliferation or had toxic effects and inhibited PBMC proliferation was extended to further antisense sequences both of TGF-β2 and other genes as detailed in the following examples 2–7.

The sequences of the oligonucleotides related with TGF-β1 are listed in FIG. 3 for the sake of ease of readability.

For certain applications, including, but not limited to application in dividing cells, including tumor cells, nucleic acid or functional or structural analogs or effective derivatives thereof according to the invention were coupled to folic acid, either at one of the carboxy-groups or at one of the nitrogen atoms of the folic acid.

Furthermore, for certain applications, nucleic acid or functional or structural analogs or effective derivatives thereof according to the invention are mixed with and/or coupled to hormones, steroid hormones such as oestrogen, progesterone, corticosteroids, mineralocorticoids, androgens, phospholipids, peptides, proteoglycans, glycolipids and derivatives therefrom. Preferably, a coupling occurs at $R^2$ and/or $R^3$ of FIGS. 1 and 2.

EXAMPLE 2 p53 Antisense Nucleic Acids (FIG. 3 Shows the Respective Oligonucleotides)

p53 is a tumor suppressor gene that negatively regulates cell proliferation. Certain mutations in the gene can alter the function of p53 in such a way that it becomes an oncogene. The effects of p53 antisense oligodeoxynucleotides on cells containing wild type p53 was analyzed and subsequently also the effect of these sequences on cells with mutated p53.

In cells with wild type p53 effective antisense nucleic acids will lead to downregulation of the wild type p53 protein and thus to enhanced proliferation of the treated cells Molecules according to the invention are named p53-1–p53-33 (SEQ ID NOS: 74–106). Noneffective p53 antisense sequences were named p53-N-1–p53-N-18. Toxic sequences, which inhibited proliferation instead of enhancing it as do effective p53 antisense sequences were named p53-T-1–p53-T-29 (SEQ ID NOS: 125–153).

Normal human fibroblasts were grown in RPMI medium supplemented with 5% fetal calf serum (FCS) and 2500 cell/well were plated into 96-well microtiter plates. Antisense phosphorothioate oligonucleotides were added at 2 µM concentration after 2 h.

Two assays to determine cell proliferation were performed:

To determine 3H-thymidine incorporation, cells were incubated before harvesting with 0.15 µCi 3H-thymidine/well for 6 h. Cells were lysed by freezing, spotted onto glass filters and the amount of incorporated tritium was determined by liquid scintillation counting.

To determine cell number, cells were stained with trypan blue and counted in a Neubauer counting chamber.

Surprisingly, only treatment of cells with antisense sequences according to the invention (p53-1–p53-33) (SEQ ID NOS: 74–105) resulted in an increase in thymidine incorporation to between 3- and 9-fold.

In contrast, treatment with noneffective sequences (p53-N-1–p53-N-18) (SEQ ID NOS: 107–124) did not result in significant alterations in thymidine incorporation.

Furthermore, treatment with toxic antisense p53 sequences (p53-T-1–p53-T-29) (SEQ ID NOS: 125–153) resulted in a decrease in proliferation instead of an increase.

In summary, the 33 antisense sequences according to the invention resulted in effective downregulation of negative growth control by p53 and increased cell proliferation, while the 47 other antisense sequences had either no significant effect on cell proliferation or even suppressed cell proliferation.

EXAMPLE 3
junB Antisense Nucleic Acids (FIG. 3 Shows the Respective Oligonucleotides)

junB and junD, two genes encoding transcription factors of the jun gene family are negative regulators of cell growth, like p53. The effects of different junB and junD antisense oligodeoxynucleotides was analyzed.

Effective junB and JunD antisense nucleic acids will lead to downregulation of the JunB an JunD proteins respectively and thus to enhanced proliferation of the treated cells. Antisense molecules according to the invention are named JunB-1–JunB-19 (SEQ ID NOS: 154–172) and JunD-1–JunD-31 (SEQ ID NOS: 173–203). Noneffective junB antisense sequences were named JunB-N-1–JunB-N-57 (SEQ ID NOS: 204–206). Toxic sequences, which inhibited proliferation instead of enhancing it were named JunB-T-1–JunB-T-20 (SEQ ID NOS: 261–280) and JunD-T-1–JunD-T-17 (SEQ ID NOS: 281–297).

Normal human fibroblasts were grown in RPMI medium supplemented with 5t fetal calf serum (FCS) and 2500 cell/well were plated into 96-well microtiter plates. Antisense phosphorothioate oligonucleotides were added at 2 $\mu$M concentration after 2 h.

Two assays to determine cell proliferation were performed:

To determine 3H-thymidine incorporation, cells were incubated before harvesting with 0.15 $\mu$Ci 3H-thymidine/well for 6 h. Cells were lysed by freezing, spotted onto glass filters and the amount of incorporated tritium was determined by liquid scintillation counting.

To determine cell number, cells were stained with trypan blue and counted in a Neubauer counting chamber.

Surprisingly, again only treatment of cells with antisense sequences according to the invention (JunB-1–JunB-19 (SEQ ID NOS: 154–172) and JunD1–JunD31 (SEQ ID NOS: 173–203)) resulted in an increase in thymidine incorporation to between 2- and 7-fold.

In contrast, treatment with noneffective sequences (JunB-N-1–JunB-N-57) (SEQ ID NOS: 204–260), did not result in significant alterations in thymidine incorporation.

Furthermore, treatment with toxic antisense junB or JunD sequences (JunB-T-1–JunB-T-20 (SEQ ID NOS: 261–280) and JunD-T-1–JunD-T-17) (SEQ ID NOS: 281–297) resulted in a decrease in proliferation instead of an increase.

In summary, the 50 antisense sequences according to the invention resulted in effective downregulation of negative growth control by JunB and JunD, while the 94 other antisense sequences had either no significant effect on cell proliferation or were even toxic.

EXAMPLE 4
(FIG. 3 Shows the Respective Oligonucleotides)

erbB-2, is a transmembrane molecule with an intracellular tyrosine kinase activity that is amplified and/or overexpressed by carcinoma cells in a variety of neoplasms including breast cancer, lung cancer, oesophageal and gastric cancer, bile duct carcinoma, bladder cancer, pancreatic cancer and ovarian cancer.

In several of these tumors, an amplification and overexpression of the c-erbB-2 gene in the tumor tissue has been shown to correlate with a poor clinical prognosis. Overexpression of p185erbB-2 in non-small-cell lung carcinoma has been shown to impart resistance to a number of chemotherapeutic agents.

Effective erbB-2 antisense nucleic acids will lead to downregulation of the erbB-2 protein and in overexpressing tumor cell lines will lead to reduced cell proliferation of the treated cells. Antisense molecules according to the invention are named erbB-2-1–erbB-2-83 (SEQ ID NOS: 298–380). Noneffective erbB-2 antisense sequences were named erbB-2-N-1–erbB-2-N-95 (SEQ ID NOS: 381–475).

erbB-2 overexpressing SK-Br-3 human mammary carcinoma cells were grown in RPMI medium supplemented with 5% fetal calf serum (FCS) and 2500 cell/well were plated into 96-well microtiter plates. Antisense phosphorothioate oligonucleotides were added at 2 $\mu$M concentration after 2 h.

To determine erbB-2 protein expression cells were harvested with a cell scraper and subjected to ELISA protein determination.

Only treatment of cells with antisense sequences according to the invention (erbB-2-1–erbB-2-83) (SEQ ID NOS: 298–380) resulted in a significant reduction in erbB-2 protein expression by 40–95%.

In contrast, treatment with noneffeective sequences (erbB-2-N-1–erbB-2-N-95) (SEQ ID NOS: 381–475) did not result in significant alterations in erbB-2 protein expression.

To determine cell number, cells were stained with trypan blue and counted in a Neubauer counting chamber.

Only treatment of cells with antisense sequences according to the invention (erbB-2-1–erbB-2-83) (SEQ ID NOS: 298–380) resulted in a reduction in cell number by 35–70%.

In contrast, treatment with noneffective sequences (erbB-2-N-1–erbB-2-N-95) (SEQ ID NOS: 381–475) did not result in significant alterations in cell proliferation.

erbB-2 antisense sequences were shown in FIGS. 3–8 to 3–11

EXAMPLE 5
(FIG. 3 Shows the Respective Oligonucleotides)

The c-fos gene encodes an immediate early gene type transcription factor. Effective c-fos antisense nucleic acids will lead to downregulation of the c-Fos protein.

Antisense molecules according to the invention are named c-fos-1–c-fos-31 (SEQ ID NOS: 476–506). Noneffective c-fos antisense sequences were named c-fos-N-1–c-fos-N-12 (SEQ ID NOS: 507–518).

Normal human fibroblasts were grown in RPMI medium supplemented with 5% fetal calf serum (FCS) and 2500 cell/well were plated into 96-well microtiter plates. Antisense phosphorothioate oligonucleotides were added at 2 $\mu$M concentration after 2 h.

Expression of the c-Fos protein was determined by ELISA in cell lysates.

Only treatment of cells with antisene sequences according to the invention (c-fos-1–c-fos-31) (SEQ ID NOS: 476–506) resulted in a significant reduction in c-fos protein expression by 45–95%.

In contrast, treatment with noneffective sequences (c-fos-N-1–c-fos-N-12) (SEQ ID NOS: 507–518) did not result in significant alterations in c-Fos protein expression.

EXAMPLE 6
(FIG. 3 Shows the Respective Oligonucleotides)

TGF-$\beta$12, like TGF-$\beta$1 is a member of the transforming growth factor-$\beta$ family of cytokines.

Overexpression of TGF-$\beta$1 and TGF-$\beta$2 is linked to malignant progression, immunosuppression and escape of the tumors from surveillance by the immune system.

Effective TGF-β2 antisense nucleic acids will lead to downregulation of the TGF-β2 growth factor.

Antisense molecules according to the invention are named TGF-β2-1–TGF-β2-38 (SEQ ID NOS: 519–556. Noneffective TGF-β2 antisense sequences were named TGF-β2-N-1–TGF-β2-N-40) (SEQ ID NOS: 557–596).

TGF-B2 overexpressing tumor cells were grown in RPMI medium supplemented with 5% fetal calf serum (FCS) and 2500 cell/well were plated into 96-well microtiter plates. Antisense phosphorothioate oligonucleotides were added at 2 µM concentration after 2 h.

TGF-β2 protein expression was determined by ELISA, both in the supernatant and in cell lysates.

Only treatment of cells with antisense sequences according to the invention (TGF-β2-1–TGF-β2-38)) (SEQ ID NOS: 519–556) resulted in a significant reduction in TGF-β2 protein expression by 35–80%.

In contrast, treatment with noneffective sequences (TGF-2-N-1–TGF-β2-N-40)) (SEQ ID NOS: 557–596) did not result in significant alterations in TGF-β2 protein expression.

EXAMPLE 7
(FIG. 3 Shows the Respective Oligonucleotides)

rb Antisense Nucleic Acids rb is a tumor suppressor gene that negatively regulates cell proliferation. The effects of rb antisense oligodeoxynucleotides on cells containing wild type rb was analyzed.

In cells with wild type rb effective antisense nucleic acids will lead to downregulation of the wild type rb protein and thus to enhanced proliferation of the treated cells. Molecules according to the invention are named rb-1–rb-45 (SEQ ID NOS: 597–641). Noneffective rb antisense sequences were named -1–rb-N-168) (SEQ ID NOS: 642–809). Toxic sequences, which inhibited proliferation instead of enhancing it as do effective rb antisense sequences were named rb-T-1–rb-T-16) (SEQ ID NOS: 810–825).

Normal human fibroblasts were grown in RPMI medium supplemented with 5% fetal calf serum (FCS) and 2500 cell/well were plated into 96-well microtiter plates. Antisense phosphorothioate oligonucleotides were added at 2 µM concentration after 2 h.

Two assays to determine cell proliferation were performed:

To determine 3H-thymidine incorporation, cells were incubated before harvesting with 0.15 µCi 3H-thymidine/well for 6 h. Cells were lysed by freezing, spotted onto glass filters and the amount of incorporated tritium was determined by liquid scintillation counting.

To determine cell number, cells were stained with trypan blue and counted in a Neubauer counting chamber.

Surprisingly, only treatment of cells with antisense sequences according to the invention (rb-1–rb-45) (SEQ ID NOS: 597–641) resulted in an increase in thymidine incorporation to between 2- and 6-fold.

In contrast, treatment with noneffective sequences (rb-N-1–rb-N-168) (SEQ ID NOS: 642–809) did not result in significant alterations in thymidine incorporation.

Furthermore, treatment with toxic antisense rb sequences (rb-T-1–rb-T-16) (SEQ ID NOS: 810–825) resulted in a decrease in proliferation instead of an increase.

In summary, the 45 antisense sequences according to the invention resulted in effective downregulation of negative growth control by rb and increased cell proliferation, while the 184 other antisense sequences had either no significant effect on cell proliferation or even suppressed cell proliferation.

EXAMPLE 8

Oligonucleotide sequences according to the invention were synthesized with various different backbone modifications:

Exemplary results are given below.

For the sequence erbB-2–42: CATCTGGAAACTTCCAGATG (SEQ ID NO: 339)

the following chemical modifications were tested in erbB-2 overexpressing carcinoma cells:

1. S-ODN erbB-2-42 (i.e. all backbone linkages were thioate modifications).

C-pS-A-pS-T-pS-C-pS-T-pS-G-pS-G-pS-A-pS-A-pS-A-pS-C-pS-T-pS-T-pS-C-pS-C-pS-A-pS-G-pS-A-pS-T-pS-G

2. Me-ODN/S-ODN/Me-ODN erbB-2-42 (i.e. Linkages at the 5' and 3' end were methylphosphonate linkages while linkages in the middle were thioate modifications as follows):

C-pMe-A-pMe-T-pS-C-pS-T-pS-G-pS-G-pS-A-pS-A-pS-A-pS-C-pS-T-pS-T-pS-C-pS-C-pS-A-pS-G-pS-A-pMe-T-pMe-G or

C-pMe-A-pMe-T-pMe-C-pS-T-pS-G-pS-G-pS-A-pS-A-pS-A-pS-C-pS-T-pS-T-pS-C-pS-C-pS-A-pS-G-pMe-A-pMe-T-pMe-G or

C-pMe-A-pMe-T-pMe-C-pMe-T-pS-G-pS-G-pS-A-pS-A-pS-A-pS-C-pS-T-pS-T-pS-C-pS-C-pS-A-pMe-G-pMe-A-pMe-T-pMe-G or

C-pMe-A-pMe-T-pMe-C-pMe-T-pMe-G-pMe-G-pS-A-pS-A-pS-A-pS-C-pS-T-pS-T-pS-C-pMe-C-pMe-A-pMe-G-pMe-A-pMe-T-pMe-G

3. Me-ODN/S-ODN erbB-2-42 (i.e. Linkages at the 5' end were methylphosphonate linkages while linkages at the 3' were thioate modifications as follows):

C-pMe-A-pMe-T-pMe-C-pMe-T-pMe-G-pMe-G-pMe-A-pMe-A-pMe-A-pS-C-pS-T-pS-T-pS-C-pS-C-pS-A-pS-G-pS-A-pS-T-pS-G

4. S-ODN/Me-ODN erbB-2-42 (i.e. Linkages at the 5' end were methylphosphonate linkages while linkages at the 3' were thioate modifications as follows):

C-pS-A-pS-T-pS-C-pS-T-pS-G-pS-G-pS-A-pS-A-pS-A-pMe-C-pMe-T-pMe-T-pMe-C-pMe-C-pMe-A-pMe-G-pMe-A-pMe-T-pMe-G

5. Me-ODN erbB-2-42 (i.e. linkages methylphosphonate linkages):

C-pMe-A-pMe-T-pMe-C-pMe-T-pMe-G-pMe-G-pMe-A-pMe-A-pMe-A-C-pMe-T-pMe-T-pMe-C-pMe-C-pMe-A-pMe-G-pMe-A-pMe-T-pMe-G 6. pN/S-ODN/pN erbB-2-42 (i.e. Linkages at the 5' and 3' end were phosphoramidate linkages while linkages in the middle were thioate modifications as follows):

C-pN-A-pN-T-pS-C-pS-T-pS-G-pS-G-pS-A-pS-A-pS-A-pS-C-pS-T-pS-T-pS-C-pS-C-pS-A-pS-G-pS-A-pN-T-pN-G or

C-pN-A-pN-T-pN-C-pS-T-pS-G-pS-G-pS-A-pS-A-pS-A-pS-C-pS-T-pS-T-pS-C-pS-C-pS-A-pS-G-pN-A-pN-T-pN-G or

C-pN-A-pN-T-pN-C-pN-T-pS-G-pS-G-pS-A-pS-A-pS-A-pS-C-pS-T-pS-T-pS-C-pS-C-pS-A-pN-G-pN-A-pN-T-pN-G or

C-pN-A-pN-T-pN-C-pN-T-pN-G-pN-G-pS-A-pS-A-pS-A-pS-C-pS-T-pS-T-pS-C-pN-C-pN-A-pN-G-pN-A-pN-T-pN-G where
pS stands for substitution of one of the non-bridging oxygen atoms of the backbone linkage with a sulfur atom, while pMe stands for substitution of one of the non-bridging oxygen atoms of the backbone linkage with a methyl group. pN stands for a N3'->P5' phosphoramidate linkage.
Also a combination of linkages (N-pS-N-pO-N-pO-N)$_n$-[pS-N]$_m$ wherein n=1–10 and m=0–6 where N stand for any nucleotide or structural or functional analog or derivative thereof.

While the Me-ODN backbone modification strongly reduced the erbB-2 activity of the erbB-2-42 (SEQ ID NO: 339) sequence to less than 20%, backbone modifications 1.–4. had strong erbB-2 inhibitory capacity with an inhibition of erbB-2 protein expression by between 78% and 89% at 2 µM concentration at 48 h after the beginning of treatment of overexpressing carcinoma cells.

While the pure S-ODN had the highest suppression capacity with 89%, the Me-ODN/S-ODN/Me-ODN as well as the Me-ODN/S-ODN and S-ODN/Me-ODN and pN/S-ODN/pN, displayed reduced protein binding and when tested for complement activation, showed reduced complement activation. These characteristics are advantageous for certain applications e.g. intravenous systemic application in vivo.

EXAMPLE 9

Similar effects were obtained when testing other sequences according to the invention with the above backbone modifications.

Inhibition of TGF-beta-1 gene expression with the effective sequences for TGF-beta-1 according to the invention was highest with S-ODN and the Me-ODN/S-ODN/Me-ODN backbone modifications and lowest with the Me-ODN modification, while protein binding and complement activation were reduced in sequences containing Me-ODN linkages.

EXAMPLE 10

Surprisingly, effectivity of sequences according to the invention was significantly improved in various cell types by coupling nucleic acids according to the invention to folic acid:

erbB-2 inhibitory capacity which was relatively low after 24 h compared to 48 h with an inhibition of erbB-2 protein synthesis by 24–37% was markedly increased by coupling sequences according to the invention to folic acid to 48–62% at 2 µM concentration 24 h after the beginning of treatment of overexpressing carcinoma cells.

Similar effects were achieved by coupling sequences according to the invention to folic acid derivatives including aminopterin and amethopterin.

EXAMPLE 11

Surprisingly, effectivity of sequences according to the invention was strongly improved by coupling oligonucleotides according to the invention to cortisol:

Cellular uptake and inhibitory capacity of sequences according to the invention including sequences for TGF-beta-1, TGF-beta-2, c-fos, p53, erbB-2, rb, c-fos, junB, junD, c-jun, MIP-1 alpha, JAK-2, bcl-2 and were markedly increased by coupling cortisol either to the 3' or 5' hydroxyl groups of oligonucleotide sequences according to the invention.

EXAMPLE 12

Effectivity of sequences according to the invention was also strongly improved in various cell types by coupling nucleic acids according to the invention to or mixing them with other steroid hormones and their derivatives, including oestrogens, anti-oestrogens, prednisone, prednisolone, androgens, anti-androgens, gestagenes like progesterone as well as peptides, proteoglycans, glycolipids, phospholipids and derivatives therefrom.

Androgens, particularly androstendion and testosterone, as well as anti-androgens, including cyproteronacetate, flutamide, anandrone, linked to the nucleic acids increased effectiveness of the molecules in various cell types including prostatic carcinoma cells.

Oestrogens, anti-oestrogens and their derivatives, including fosfestrol, toremifen, ethinyloestradiole, diethylstilboestole and the oestradiole derivatives oestradiol-benzoate, oestradiol-valerinate and oestradiol-undecylate, as well as progesterone and its derivatives, including medroxyprogestroneacetate and megestrolacetate linked to the oligonucleotides strongly enhanced activity of the molecules according to the invention in various cell types including mammary carcinoma cells.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6972171B1). An electronic copy of the "Sequence Listing" will also be available from the USPTO upon request and payment of the fee set forth in 37 CFR 1.19(b)(3).

What is claimed is:

1. A method for the selection and preparation of an effective antisense oligonucleotide for a nucleic acid comprising the steps of
designing an antisense oligonucleotide corresponding to a target nucleic acid sequence, such that
a) the antisense oligonucleotide comprises at least 8 nucleic acid residues,
b) the antisense oligonucleotide comprises a maximum of twelve elements, each the twelve elements being a nucleotide capable of forming three hydrogen bonds to a cytosine base,
c) the antisense oligonucleotide does not contain four or more consecutive elements,
d) the antisense oligonucleotide does not contain two or more series of three consecutive elements, and
e) the ratio of residues forming two hydrogen bonds each with the target nucleic acid sequence with respect to residues forming three hydrogen bonds each with the target nucleic acid sequence is $$\frac{3H\text{-bond-}R}{3H\text{-bond-}R + 2H\text{-bond-}R} \geq 0.29$$

wherein
3H-bond-R=residues forming three hydrogen bonds per residue and
2H-bond-R=residues forming two hydrogen bonds per residue,
generating the designed antisense oligonucleotide, and
synthesizing the generated antisense oligonucleotide.

2. The method according to claim 1, wherein the four or more consecutive elements not contained in the antisense oligonucleotide are each guanosine.

3. The method according to claim 1, wherein the three consecutive elements in the two or more series not contained in the antisense oligonucleotide are each guanosine.

4. The method according to claim 1, wherein the generated oligonucleotide complies with the following specification $$\frac{3H\text{-bond-}R}{3H\text{-bond-}R + 2H\text{-bond-}R} = 0.33 \text{ to } 0.86.$$

5. The method according to claim 1, wherein the generated oligonucleotides are modified for higher nuclease resistance than naturally occurring oligo- or polynucleotides.

6. The method according to claim 5, wherein the generated oligonucleotides are modified at the bases, the sugars or the linkages of the oligonucleotides, preferably by phosphorothioate (S-ODN) internucleotide linkages, and/or methylphosphonate internucleotide linkages, N'3->P5' phosphoramidate linkages, peptide linkages or 2'-methoxyethoxy modifications of the sugar or modifications of the bases.

7. The method according to claim 6, wherein the oligonucleotide has at least two different types of modifications.

8. The method according to claim 1, wherein the oligonucleotides are reacted with folic acid, hormones such as steroid hormones or corticosteroids or derivatives thereof by linking the oligonucleotides covalently to or mixing with folic acid, hormones such as steroid hormones or corticosteroids, peptides, proteoglycans, glycolipids or phospholipids.

9. An antisense oligonucleotide consisting of SEQ ID NO: 1754.

* * * * *